(12) United States Patent
Beebe et al.

(10) Patent No.: US 10,564,077 B2
(45) Date of Patent: Feb. 18, 2020

(54) DEVICE FOR AND METHOD OF ISOLATING AND ANALYZING A FRACTION IN A BIOLOGICAL SAMPLE

(71) Applicant: Wisconsin Alumni Research Foundation, Madison, WI (US)

(72) Inventors: David J. Beebe, Monona, WI (US); Joshua M. Lang, Madison, WI (US); Benjamin P. Casavant, Madison, WI (US); Scott M. Berry, Madison, WI (US); Lindsay N. Strotman, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 94 days.

(21) Appl. No.: 13/832,860

(22) Filed: Mar. 15, 2013

(65) Prior Publication Data

US 2014/0065622 A1    Mar. 6, 2014

Related U.S. Application Data

(63) Continuation-in-part of application No. 13/604,192, filed on Sep. 5, 2012, now Pat. No. 8,728,411, and a continuation-in-part of application No. 13/737,448, filed on Jan. 9, 2013, now Pat. No. 9,766,166.

(51) Int. Cl.
| | |
|---|---|
| *G01N 1/40* | (2006.01) |
| *C12N 15/10* | (2006.01) |
| *G01N 1/34* | (2006.01) |
| *C12Q 1/68* | (2018.01) |
| *G01N 33/543* | (2006.01) |

(52) U.S. Cl.
CPC ......... *G01N 1/405* (2013.01); *C12N 15/1013* (2013.01); *C12Q 1/68* (2013.01); *G01N 1/34* (2013.01); *G01N 33/543* (2013.01); *G01N 33/54326* (2013.01)

(58) Field of Classification Search
None
See application file for complete search history.

(56) References Cited

U.S. PATENT DOCUMENTS

| | | | |
|---|---|---|---|
| 5,279,936 A | 1/1994 | Vorpahl | |
| 6,117,398 A | 9/2000 | Bienhaus et al. | |
| 7,820,454 B2 | 10/2010 | Su et al. | |
| 8,017,340 B2 | 9/2011 | Collier et al. | |
| 8,048,633 B2 | 11/2011 | Collier et al. | |
| 8,304,188 B2 | 11/2012 | Kelso et al. | |
| 2004/0224380 A1 | 11/2004 | Chou et al. | |
| 2005/0112601 A1 | 5/2005 | Hassibi et al. | |
| 2005/0208548 A1 | 9/2005 | Block et al. | |
| 2006/0024824 A1 | 2/2006 | Woodside et al. | |
| 2007/0042396 A1 | 2/2007 | Park et al. | |
| 2008/0124779 A1 | 5/2008 | Oh et al. | |
| 2008/0226500 A1 | 9/2008 | Shikida et al. | |
| 2009/0191594 A1 | 7/2009 | Ohashi | |
| 2009/0246782 A1 | 10/2009 | Kelso et al. | |
| 2010/0273142 A1 | 10/2010 | Prins et al. | |
| 2010/0291666 A1 | 11/2010 | Collier et al. | |
| 2012/0094275 A1 | 4/2012 | Rao et al. | |
| 2012/0178096 A1* | 7/2012 | Beebe et al. | 435/6.19 |

FOREIGN PATENT DOCUMENTS

| | | |
|---|---|---|
| JP | 02255074 A * | 10/1990 |
| WO | 2006071770 | 7/2006 |

OTHER PUBLICATIONS

"Development of an enzymatic reaction device using magnetic bead-cluster handling", Shikida et al, J. Micromech. Microeng. 16 (2006) 1875-1883.
"Controlled microfluidic interfaces", Atencia et al, Nature, vol. 437, Sep. 29, 2005, 648-655.
"Using wettability and interfacial tension to handle droplets of magnetic beads in a micro-chemical-analysis system", Shikida et al, Sensors and Actuators B 113 (2006) 563-569.
"Droplet-based gene expression analysis using a device with magnetic force-based-droplet-handling system", Okochi et al, Journal of Bioscience and Bioengineering, vol. 109, No. 2, 2010, 193-197.
"On-chip polymerase chain reaction microdevice employing a magnetic droplet-manipulation system", Tsuchiya et al, Sensors and Actuators B 130 (2008) 583-588.

(Continued)

*Primary Examiner* — Allison M Fox
*Assistant Examiner* — Qing Xu
(74) *Attorney, Agent, or Firm* — Boyle Fredrickson, S.C.

(57) ABSTRACT

A device and a method are provided for isolating a fraction in a biological sample. The fraction is bound to solid phase substrate to define a fraction-bound solid phase substrate. The device includes an input zone for receiving the biological sample therein to capture a desired fraction of the biological sample. A force is provided that is generally perpendicular to gravity. The force is movable between a first position adjacent the input zone multiple other positions adjacent various purification, protein analysis, separation and extraction zones. The force captures the fraction-bound solid phase substrate and the fraction-bound solid phase substrate moves from the input zone to the other zones to perform a multi-step assay on the isolated fraction within the device.

18 Claims, 21 Drawing Sheets

(56) References Cited

OTHER PUBLICATIONS

"A novel Real Time micro PCR based Point-of-Care device for *Salmonella* detection in human clinical samples", Verdoy et al, Biosensors and Bioelectronics 332 (2012) 259-265.

"Forced motion of a probe particle near the colloidal glass transition", Habdas et al, Europhys. Lett., 67(3), pp. 477-583 (2004).

"Development of a Low-Resource RNA Extraction Cassette Based on Surface Tension Valves", Bordelon et al, Appl. Mater. Interfaces 2011, 3, 2161-2168.

\* cited by examiner

DEVICE FOR AND METHOD OF ISOLATING AND ANALYZING A FRACTION IN A BIOLOGICAL SAMPLE

CROSS-REFERENCE TO RELATED APPLICATIONS

This application claims priority as a continuation-in-part of U.S. Non-Provisional patent application Ser. No. 13/604,192, filed on Sep. 5, 2012, and as a continuation-in-part of U.S. Non-Provisional patent application Ser. No. 13/737,448, filed on Jan. 9, 2013, the entirety of which are expressly incorporated by reference herein.

REFERENCE TO GOVERNMENT GRANT

This invention was made with government support under W81XWH-09-1-0192 awarded by the ARMY/MRMC. The government has certain rights in the invention.

FIELD OF THE INVENTION

The present invention relates generally to the isolation of a fraction from a biological sample, and in particular, to a device and a method for more effectively isolating cells from complex biological backgrounds so as to reduce sample loss associated therewith enabling assays to be performed on the isolated cells.

BACKGROUND AND SUMMARY OF THE INVENTION

The isolation of a specific subset of cells from a heterogeneous population of cells is necessary for a range of research and diagnostic tools. For example, isolation of circulating tumor cells (CTCs) from a buffy coat formed from a patient blood draw has shown clinical relevance. As is known, however, CTCs within the circulation of patients with metastatic cancer are very rare. More specifically, there is approximately one CTC per billion background cells. Further, the prognostically relevant bar for determining overall survival and disease-free progression of a patient is 5 CTCs per 7.5 milliliters (mLs) of whole blood. As such, CTC capture is an isolation method requiring both high sensitivity (5 cells) and high specificity (7.5 billion background cells). In addition, once captured, clinically relevant cellular analyses must be performed on the CTCs downstream of isolation.

While offering the flexibility to perform a wide range of downstream assays, macroscale methods to perform MC isolation have been found to be unsatisfactory. More specifically, macroscale methods to isolate these types of cells often require long, expensive and laborious procedures that may result in significant sample loss due to wasteful transfer steps or centrifugation and re-suspension steps, Capturing rare cells such as CTCs, which occur at frequencies on the order of 5-50 cells per 7.5 mL blood sample, is not feasible using traditional macroscale methods, as the loss of a single cell can represent up to a 20% loss of sample.

In order to overcome cell loss associated with the macroscale methods, heretofore described, microfluidic methods have arisen. Microfluidics offers novel solutions to the challenges of macroscale methods by providing a highly controlled, low-volume platform that can quickly and efficiently isolate cells. Further, microfluidic platforms offer sensitivity and specificity that is unattainable using current macroscale systems. Established microfluidic methods include functionalized micropost arrays, patterned surfaces and microfluidic systems that leverage density or other physical characteristics to isolate cells of interest from non-target cells.

In particular, the ability to use functionalized paramagnetic particles (PMPs) in microfluidic systems to isolate analyte of interest has expanded the utility of isolation methods across a range of platforms. One of PMPs advantages is that the particles are flexible for use in many system configurations since only a magnet is required for actuation and analyte isolation.

The ways to isolate an analyte of interest from a given sample can further divided into two basic methods. First, in the current primary method for using PMPs, the PMPs are held stationary while fluid is washed over the substrate to remove the background sample and any contaminants. Limitations of this popular method include the loss of the original input sample, allowing only a single effective isolation per sample, and the inefficiency of dilution-based sample preparation techniques, thereby necessitating multiple washes to effectively remove contaminants and leading to lengthy workflows. Second, recent work has demonstrated the ability to remove the PMPs from the original sample of interest using exclusion-based methods. These methods generally leverage gravitational forces or the dominance of surface tension at the microscale to position original samples and physically drag the PMPs out of the input sample along the surface of a device through some immiscible phase (e.g., air or oil) and into a second aqueous phase. These methods have been highly effective at isolating analyte with high specificity and selectivity. Further, these methods have been beneficial for their elegant workflow since isolation can be performed in a matter of seconds. Though effective, problems for these methods exist in the need for an immiscible fluid (oil) that can complicate both the fabrication and use of these techniques on larger scales and the function of 'dragging' particles along a surface resulting in a friction-based loss of sample.

By way of a specific example of a microfluidic system of this type, Beebe et al., United States Patent Application Publication No. 2011/0213133, incorporated by reference herein in its entirety, discloses a device and a method for facilitating extraction of a fraction from a biological sample. The biological sample includes non-desired material and a fraction-bound solid phase substrate. The device includes an input zone for receiving the biological sample therein and a second zone for receiving an isolation buffer therein. An output zone receives a reagent therein. A force is movable between a first position adjacent the input zone and a second position adjacent the output zone. The force urges the fraction-bound solid phase substrate from the input zone, through the second zone and into the output zone.

While functional for its intended purpose, the device and method disclosed in the Beebe et al., '133 publication has certain limitations. For example, when the biological sample contains large particulates, debris, precipitates, or other cells that settle out of solution, the efficiency of the recovery and the overall purity of the fraction-bound solid phase substrate decreases as a result of non-desired material impeding the operational path of the fraction-bound solid phase substrate.

In addition, concerning the downstream analysis of the CTCs after isolation, the methods for isolating DNA, RNA, and proteins from complex biological samples are some of the most crucial steps in molecular biology. However, these methods are often overlooked within the biological sample processing workflow. As the throughput of downstream analytical techniques have increased, sample preparation methods have become a limiting factor in overall throughput. Many of the most used methods for sample preparation are very time consuming and can involve many steps including substrate binding, multiple wash steps, dilutions, or other processes that can result in loss of sample or dramatic increases in assay time.

More particularly, when samples of the CTCs of interest are obtained, the current techniques that exist for extraction and purification of RNA and DNA from a single sample are not specifically applicable to analysis of rare cell populations (<1000). This is significantly limiting as biological systems are starting to address these smaller cell populations to understand larger biological processes (e.g. stem cells, CTCs, etc.). The one currently existing assay for circulating tumor cells CTCs is only valid for cell enumeration, without cell purification or nucleic acid extraction/analysis. Other platforms have attempted to capture and analyze CTCs with varying degrees of success. However none can perform protein, DNA and mRNA analysis in an integrated fashion and from a single sample.

Therefore, it is a primary object and feature of the present invention to provide a device and a method isolating a fraction from a biological sample.

It is a further object and feature of the present invention to provide a device and a method for isolating a fraction from a biological sample that is simpler to fabricate, easier to implement and more efficient than prior devices and methods.

It is a still a further object and feature of the present invention to provide a device and a method for isolating a fraction from a biological sample without the significant sample loss associated with prior methods, such as reducing the friction-based losses of the targeted fraction of prior devices/methods.

It is still a further object and feature of the present invention to provide a device that can achieve superior capture of the desired fraction of the biological sample, but that can also perform a comprehensive assay and/or analysis of the fraction using the device without physically contacting the biological sample that encompasses many process for analysis of the fraction including, but not limited to, cell capture, isolation/purification, protein analysis, and DNA and RNA extraction endpoints from a single sample, on as little as a single cell. The device can be used to stain the fraction of the biological sample within the device for imaging analysis, and to extract mRNA and DNA from the fraction without splitting into multiple fractions such that the integrity of the original fraction is maintained and not diluted or washed away, and can therefore be re-sampled for additional analytes. Under this object, the device can be utilized to perform a "fluid biopsy" from a simple blood draw, potentially eliminating the need to perform painful, invasive and expensive tumor biopsies.

In accordance with the present invention, a device is provided for isolating a fraction in a biological sample. The device can take various forms and in one embodiment the fraction is bound to solid phase substrate to define a fraction-bound solid phase substrate. The device includes an input zone for receiving the biological sample therein and an isolation zone for receiving an isolation fluid therein. A force, generally perpendicular to gravity, is movable between a first position adjacent the input zone and a second position adjacent the isolation zone. The force captures the fraction-bound solid phase substrate such that the fraction-hound solid phase substrate moves from the input zone to the isolation zone in response to the force moving from the first position to the second position.

The input zone is partially defined by a lower surface lying in a first plane and wherein the device further comprising a passage having a input communicating with the input zone and an output communicating with the isolation zone. The passage is partially defined by first and second walls. The first and second side walls of the passage at least partially converge from the input to the output thereof. The passage extends along an axis. The axis is vertically spaced from the first plane. The isolation zone is partially defined by a lower surface lying in a second plane, the second plane being between the first plane and the axis. It is contemplated for the force to be a magnetic field. Further, it is contemplated for the force to move from the first position to the second position along a path at least generally transverse to gravity.

In accordance with a further aspect of the present invention, a device is provided for isolating a fraction in a biological sample. The fraction is bound to a solid phase substrate to define a fraction-bound solid phase substrate. The device includes an input zone for receiving the biological sample therein. The input zone is partially defined by a lower surface lying in a first plane. An isolation zone receives an isolation fluid therein. The isolation zone is partially defined by a lower surface lying in a second plane. A passage extends along an axis and has an input communicating with the input zone and an output communicating with the isolation zone. A force captures the fraction-bound solid phase substrate. The force is generally normal to gravity and is movable between a first position adjacent the input zone and a second position adjacent the isolation zone. The captured fraction-bound solid phase substrate moves from the input zone to the isolation zone in response to the force moving from the first position to the second position.

The passage is partially defined by first and second walls. The first and second side walls converge from the input to the output thereof. The axis of the passage is vertically spaced from the first plane and the second plane is between the first plane and the axis. It is contemplated for the force to be a magnetic field. Further, it is contemplated for the force to move from the first position to the second position along a path transverse to gravity and to the force.

In accordance with another aspect of the present invention, the isolation zone can contain a fluid capable of providing an extracellular stain to the fraction bound to the solid phase substrate within the isolation zone or well.

In accordance with a still further aspect of the present invention, a method is provided of isolating a fraction in a biological sample. The method includes the step of providing a biological sample including a fraction-bound solid phase substrate and biological material in an input well. The input well is partially defined by a lower surface lying in a first plane. The fraction-bound solid phase substrate is captured with a force so as to maintain the fraction-bound solid phase substrate at a location above the lower surface of the input well. The biological material is allowed to settle towards the lower surface of the input well and the fraction-bound solid phase substrate is drawn into an isolation well through a passage with the force. The passage extends along an axis vertically spaced above the first plane.

It is contemplated for the force to be generally normal to gravity and to be a magnetic field. The force travels along a path to draw the fraction-bound solid phase substrate from the input well into the isolation well. The path is transverse to gravity. The passage has an input communicating with the input zone and an output communicating with the isolation well or zone. The passage is partially defined by first and second walls. The first and second side walls converge from the input to the output thereof. The isolation well is partially defined by a lower surface lying in a second plane. The second plane is between the first plane and the axis.

In accordance with still another aspect of the present invention, the device also optionally includes a sieve well disposed downstream from the input well, or the isolation well, if present, and joined thereto by a passage having an input communicating with the input or isolation well and an output communicating with the sieve well. The axis of the passage is vertically spaced from the first plane and the passage is partially defined by first and second walls that converge from the input to the output thereof. The sieve well is formed similarly to the isolation well and is partially defined by a lower surface lying in a third plane. The third plane is between the first plane and the axis. The sieve well also includes a separation membrane dividing the sieve well into cavities. The membrane allows for the transfer of fluid between the cavities, while retaining the target or fraction-bound solid phase substrate in the cavity connected to the output of the passage.

In accordance with a still further aspect of the present invention, a method is provided of staining a target in or fraction of a biological sample within the device in order to perform imaging analyses on the fraction within the device. The method includes the step of providing a biological sample including a fraction-bound solid phase substrate and biological material in the input well and moving the fraction using the force from the input well into one of the cavities of the sieve well. The fluid initially present in the sieve well can be used to wash the fraction or target within the sieve well, After washing, the wash fluid is withdrawn out of both cavities of the sieve well via the cavity opposite the cavity holding the fraction. The fluid can pass through the membrane disposed between the cavities in order to be withdrawn from both cavities, while the fraction is retained in the sieve well, such that the solid phase is not physically contacted during the process. A subsequent fluid, such as a fixing and/or permeabilizing fluid, can be introduced into the cavities of the sieve well in a reverse process, allowing the fluid to act upon the fraction, again without physically contacting the fraction. After fixing/permeabilizing the fraction, the fluid can be drawn out of the sieve well and subsequently replaced with a stain in order to effect the fraction and a provide visual indication to a selected component of the fixed/permeabilized fraction. The stain can be removed through the membrane and the fraction can be contacted with a wash fluid in the same manner. The process can be repeated as many times as desired to stain different intracellular components of the fraction to enable the components present in the fraction to be analyzed, such as via a proteomic imaging analysis of the stained fraction without any direct manipulation of the captured cells, minimizing cell damage and loss.

In accordance with still a further object of the present invention, the device also optionally includes a separation well disposed downstream from the input well, or the isolation or sieve well, if present, and joined thereto by a passage having an input communicating with the input well, isolation well or sieve well and an output communicating with the separation well. The axis of the passage is vertically spaced from the first plane and the passage is partially defined by first and second walls that converge from the input to the output thereof. The separation well is formed similarly to the input well and is partially defined by a lower surface lying in a fourth plane. The fourth plane is between the first plane and the axis.

The separation well is connected to a pair of passages each having an input communicating with the separation well and an output communicating with one of a pair cavities formed in an elution well. The axis of each of the passages is vertically spaced from the first plane and the passages are partially defined by first and second walls that converge from the input to the output thereof. The elution well is formed similarly to the separation well and is defined by a lower surface lying in a fifth plane. The fifth plane is between the first plane and the axis.

In accordance with a still further aspect of the present invention, a method is provided of separating the fraction into DNA and RNA fractions for analysis within the device. The fraction-bound solid phase substrate is moved into the separation well from the input well using the force described previously. In the separation well, the fraction-bound solid phase material can be repeatedly interrogated by sequentially adding components with varying chemistries to the separation well to isolate mRNA and DNA from the same sample of the fraction-bound substrate. Following mRNA binding, the force is utilized to draw the mRNA through one of the passages to the corresponding cavity of the elution well, Additionally, DNA is bound by a different component and moved by the force through the other passage to the corresponding separated cavity in the elution well. The samples of the mRNA and the DNA can then be collected from their respective elution well cavities and used for a variety of downstream assays.

In accordance with still another aspect of the present invention, the device can be utilized in a method to perform a fully integrated assay that performs cell capture, purification, protein, genomic and gene expression studies from a single sample on as few as 1-10 cells forming the target or fraction of the biological sample introduced into the device in the method.

In accordance with another embodiment of the present invention, a device is provided for isolating a target or fraction from a biological sample. The target is bound to solid phase substrate to form target bound solid phase substrate. The device includes a lower plate with an upper surface having a plurality of regions. The biological sample is receivable on a first of the regions. An upper plate has a lower surface directed to the upper surface of the lower plate. A force adjacent the upper plate attracts the target bound solid phase substrate toward the lower surface of the upper plate. At least one of the upper plate and the lower plate is movable from a first position wherein the target bound solid phase substrate in the biological sample are drawn to the lower surface of the upper plate and a second position wherein the target bound solid phase substrate are isolated from the biological sample.

The regions of the lower plate are hydrophilic and the portions of the upper surface of the outside of the regions of the lower plate are hydrophobic. The lower surface of the upper plate is also hydrophobic. The upper plate is axially movable between the first and second positions or is rotatably between the first and second positions. The upper surface of the lower plate and lower surface of the upper surface are spaced by a predetermined distance.

In accordance with a further aspect of the present invention, a method is provided for isolating a target from a biological sample. The target is bound to solid phase substrate to form target bound solid phase substrate. The method includes the steps of providing the biological sample at a region of a surface of a lower plate and positioning an upper plate in spaced relation to the lower plate. The upper plate has a lower surface directed to the upper surface of the lower plate. The target bound solid phase substrate is drawn toward the lower surface of the upper plate with a force. At least one of the lower plate and the upper plate is moved from a first position wherein the target bound solid phase substrate in the biological sample are drawn toward the lower surface of the upper plate to a second position wherein the target bound solid phase substrate are isolated from the biological sample.

The upper surface of the lower plate may include a plurality of regions that are hydrophilic. The upper surface of the lower surface outside of the regions is hydrophobic. The lower surface of the upper plate is hydrophobic. The upper plate moves along a longitudinal axis between the first and second positions or is rotatable between the first and second positions. It is contemplated to space the upper surface of the lower plate and lower surface of the upper surface by a predetermined distance.

In accordance with a still further aspect of the present invention, a method is provided for isolating a target from a biological sample. The target is bound to solid phase substrate to form target bound solid phase substrate. The method includes the step of providing the biological sample at a first region of a surface of a first plate. A fluid is deposited on a second region of the surface of the first plate. A second plate is positioned in spaced relation to the first plate. The second plate has a hydrophobic surface directed towards the surface of the first plate. The target bound solid phase substrate is drawn toward the surface of the second plate with a force. At least one of the first plate and the second plate is moved from a first position wherein the target bound solid phase substrate in the biological sample are drawn toward the surface of the second plate to a second position wherein the target bound solid phase substrate are isolated from the biological sample.

The portions of the surface of the first plate outside of the first and second regions are hydrophobic. The second plate moves along a longitudinal axis between the first and second positions or is rotatable between the first and second positions. The surface of the second plate is spaced from the surface of the first plate by a predetermined distance. It is intended for the force to be magnetic and for the target bound solid phase substrate to be received in the fluid with the at least one of the first plate and the second plate in the second position. The fluid can be selected to be able to be utilized to wash, fix, permeabilize, stain or extract RNA or DNA from the target substance, or in any combination thereof. The method may also include the step of isolating the target bound solid phase substrate from the force.

BRIEF DESCRIPTION OF THE DRAWINGS

The drawings furnished herewith illustrate a preferred construction of the present invention in which the above aspects, advantages and features are clearly disclosed as well as others which will be readily understood from the following description of the illustrated embodiments.

In the drawings.

DETAILED DESCRIPTION OF THE DRAWINGS

Figure 1:
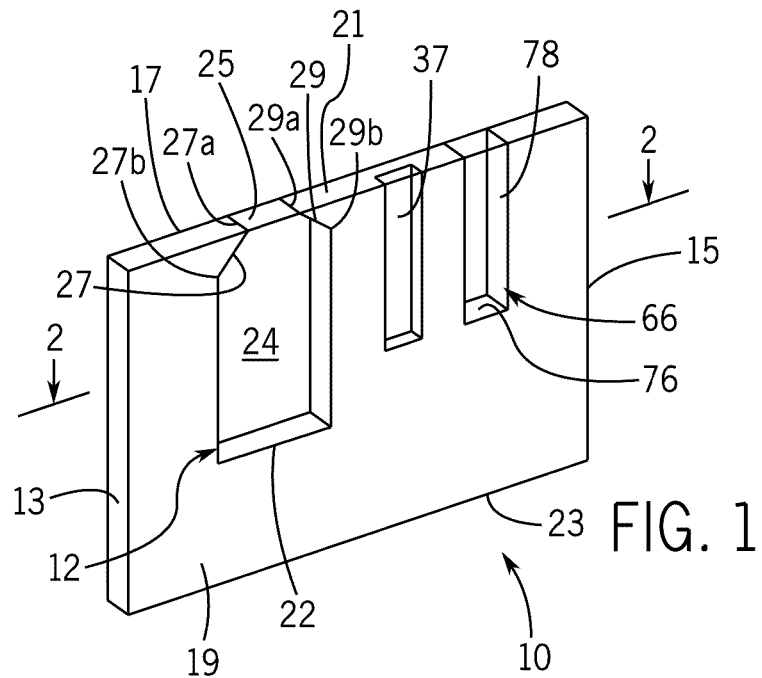
FIG. 1 is an isometric view of a first embodiment of the device in accordance with the present invention in an initial configuration.
Figure 2:
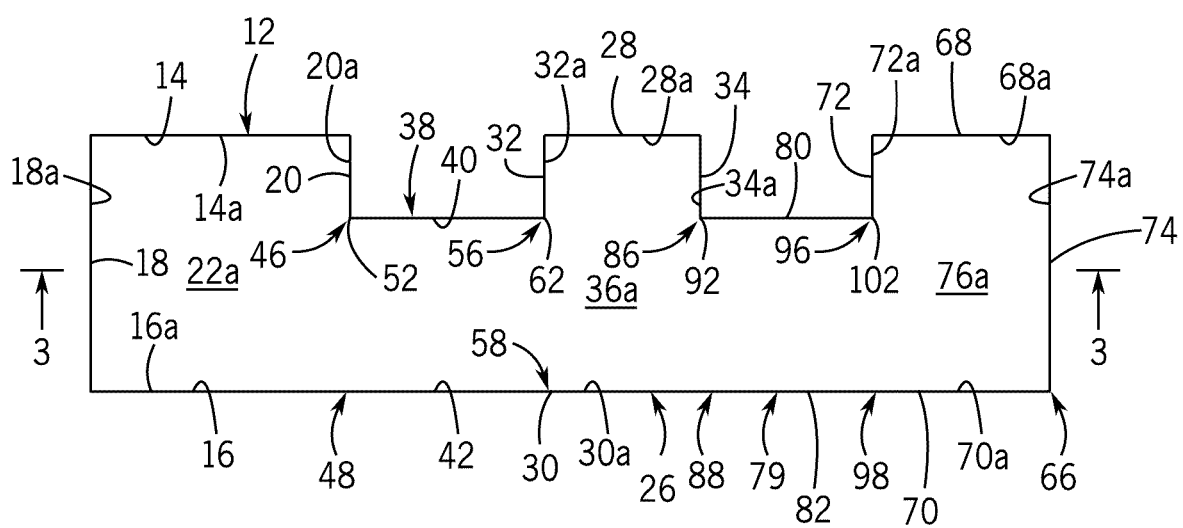
FIG. 2 is a schematic, cross-sectional view of the device of the present invention taken along line 2-2 of FIG. 1.
Figure 3:
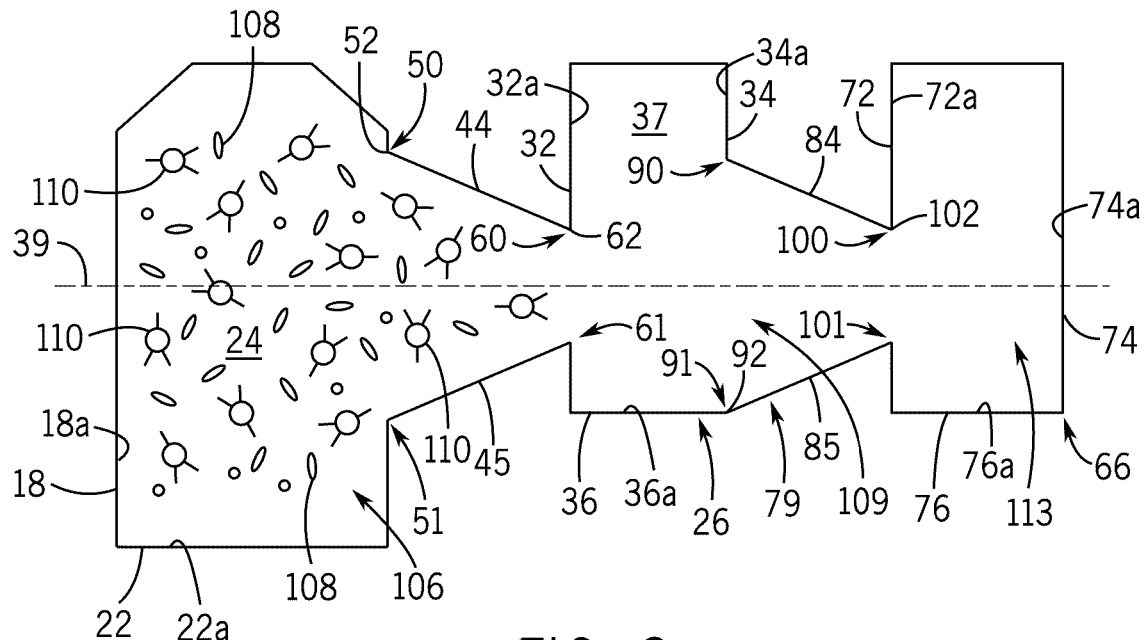
FIG. 3 is a schematic, cross-sectional view of the device of the present invention taken along line 3-3 of FIG. 2.

Referring to FIGS. 1-6, a device for extracting and purifying a fraction, such as cells, from a complex background including non-desired cells, tissue samples and other biological materials, in accordance with the present invention, is generally designated by the reference numeral 10. Device 10 includes first and second ends 13 and 15, respectively; first and second sides 17 and 19, respectively; and upper and lower surfaces 21 and 23, respectively. Other configurations are possible without deviating from the scope of the present invention.

Device 10 further includes input zone or well 12 defined by first and second sidewalls 14 and 16, respectively, first and second end walls 18 and 20, respectively, and bottom wall 22. Input well 12 includes input 25 communicating with upper surface 21 of device 10 and being partially defined by the upper edges of sidewalls 14 and 16. Input 25 to input well 12 is further defined upper edges 27a and 29a of diverging upper walls 27 and 29. Upper edges 27a and 29a of diverging upper walls 27 and 29 are generally parallel to each other and generally perpendicular to the upper edges of first and second sidewalls 14 and 16, respectively. Lower edges 27b and 29b of upper walls 27 and 29 intersect corresponding upper edges of first and second end walls 18 and 20, respectively. In the depicted embodiment, input 25 has a generally rectangular configuration, but it can be appreciated that other configurations are possible without deviating from the scope of the present invention.

Bottom wall 22 of input well 12 lies in a first plane, for reasons hereinafter described. Inner surfaces 14a and 16a of sidewalls 14 and 16, respectively, inner surfaces 18a and 20a of first and second end walls 18 and 20, respectively, and upper surface 22a of bottom wall 22 define input cavity 24 for receiving a biological sample therein. While input well 12 has a generally rectangular configuration in the depicted embodiment, other configurations are contemplated without deviating from the scope of the present invention. It can be appreciated that a user can fill input cavity 24 with the biological sample through input 25 of input well 12.

Second well 26 is provided in device 10 downstream of input well 12. Second well 26 is defined by first and second sidewalls 28 and 30, respectively, upstream wall 32, downstream wall 34 and bottom wall 36. Bottom wall 36 of second well 26 lies in a second plane vertically spaced above the first plane. Inner surfaces 28a and 30a of sidewalls 28 and 30, respectively, inner surface 32a of upstream wall 32, inner surface 34a of downstream wall 34, and upper surface 36a of bottom wall 36 define second cavity 37 for receiving a predetermined fluid therein, e.g. isolation buffer as hereinafter described. Again, although second well 26 has a generally rectangular configuration in the depicted embodiment, other configurations are contemplated without deviating from the scope of the present invention.

Input well 12 and second well 26 are interconnected by first passage 38. First channel 38 extends along an axis 39 which is vertically spaced from and above the first and second planes. First channel 38 is defined by first and second sidewalls 40 and 42, respectively, upper wall 44 and bottom wall 45. Input ends 46 and 48 of first and second sidewalls 40 and 42, respectively, of first channel 38 and input ends 50 and 51 of upper and bottom walls 44 and 45, respectively, of input channel 38 intersect end wall 20 of input well 12 so as to define input 52 to first channel 38. Output ends 56 and 58 of first and second sidewalls 40 and 42, respectively, of first channel 38 and output ends 60 and 61 of upper and bottom walls 44 and 45, respectively, of first channel 38 intersect upstream wall 32 of second well 26 so as to define output 62 of first channel 38. First and second sidewalls 40 and 42, respectively, of first channel 38 are generally parallel to each other, FIG. 2. As best seen in FIGS. 1 and 3-6, upper and bottom walls 44 and 45, respectively, respectively, of first channel 38 converge towards each other from input 52 to output 62, for reasons hereinafter described.

Device 10 further includes third zone or well 66 downstream of second well 26 and being defined by first and second sidewalls 68 and 70, respectively, upstream wall 72, downstream wall 74 and bottom wall 76. Bottom wall 76 of third well 66 lies in the second plane vertically spaced above the first plane. Inner surfaces 68a and 70a of sidewalls 68 and 70, respectively, inner surface 72a of upstream wall 72, inner surface 74a of downstream wall 74, and upper surface 76a of bottom wall 76 define output cavity 78 for receiving a predetermined fluid, e.g. a reagent, therein for reasons hereinafter described. Again, third well 66 has a generally rectangular configuration in the depicted embodiment. However, other configurations are contemplated without deviating from the scope of the present invention.

Third well 66 and second well 26 are interconnected by second channel 79. Second channel 79 extends along axis 39 and is defined by first and second sidewalls 80 and 82, respectively, upper wall 84 and bottom wall 85. Input ends 86 and 88 of first and second sidewalls 80 and 82, respectively, of second channel 79 and input ends 90 and 91 of upper and bottom walls 84 and 85, respectively, of second channel 79 intersect downstream wall 34 of second well 26 so as to define input 92 to second channel 79. Output ends 96 and 98 of first and second sidewalls 80 and 82, respectively, of second channel 79 and output ends 100 and 101 of upper and bottom walls 84 and 85, respectively, of second channel 79 intersect upstream wall 72 of third well 66 so as to define output 102 of second channel 79. First and second sidewalls 80 and 82, respectively, of second channel 79 are generally parallel to each other, FIG. 2. As best seen in FIGS. 1 and 3-6, upper and bottom walls 84 and 85, respectively, of second channel 79 converge towards each other from input 92 to output 102, for reasons hereinafter described.

In operation, it is intended to utilize device 10 to extract a fraction, such as a desired cell, nucleic acids, and/or proteins, from biological sample 106. As is known, biological sample 106 may include non-desired material 108 such as lysate, bodily fluids, forensic samples, and/or biological contaminations. In order to prepare biological sample 106 for extraction of the fraction, an appropriate reagent is added to biological sample 106 and mixed such that fraction binds to a solid phase substrate in the reagent to form fraction-bound solid phase substrate 110. It is contemplated for the solid phase substrate to be attracted to a corresponding force. For example, the solid phase substrate may be a paramagnetic material attracted to a corresponding magnetic field. Other non-magnetic mechanisms such as ultrasonic actuation or the like are contemplated as being within the scope of the present invention. Once mixed with the reagent, biological sample 106 including fraction-bound solid phase substrate 110 is deposited into input cavity 24 through input 25 of input well 12. It is noted that the reduced cross-sectional area of input 25 to input well 12 pins biological sample 106 within input cavity 24 such that inversion of device 10 will not result in biological sample 106 spilling out of input well 12 through input 25 thereof. Hence, it can be appreciated that device 10 may be rotated and/or inverted to facilitate the mixing of biological sample 106 and the reagent in input cavity 24 of input well 12 or maintain fraction-bound solid phase substrate 110 in suspension.

In addition to depositing biological sample 106 in input cavity 24 of input well 12, isolation buffer 109, such as oil or wax, is deposited in second cavity 37 of second well 26; and a desired reagent 113 is deposited in third cavity 78 of third well 66. Device 10 of the present invention relies upon the dominance of surface tension over gravity at the microscale to establish "virtual walls" between each fluid interface. This dominance of surface tension enables the side-by-side loading of fluids in the devices that is not possible on the macroscale. This phenomenon is quantified by the dimensionless Bond number:

$$Bo = \rho g L2/\gamma \qquad \text{Equation (1)}$$

wherein: Bo is the Bond number; $\rho$ is the density of a fluid; g is the acceleration of gravity; L is a characteristic length scale of the device; and $\gamma$ is the surface energy of the fluid.

A Bond number (Bo) less than 1 indicates a system n which surface tension forces are sufficiently large to marginalize the effects of gravity. For larger Bond number (Bo) devices, gravity dominance mandates positioning of the denser biological sample in input well 12 and reagent in third well 66 below the isolation buffer in second well 26, constraining device geometry into a three-dimensional architecture. Because Bond number (Bo) scales with the square of the characteristic length scale of the device ($L^2$), a reduction in device dimensions rapidly reduces the Bond number (Bo) into the surface tension-dominant regime. Microfluidic constrictions with very small characteristic length scales selectively impede liquid motion, enabling serial loading of all three device fluids (the biological sample, the isolation buffer and the reagent) into their respective wells (input well 12, second well 26 and third well 66, respectively) without intermixing or density-driven stratification. Hence, the reliance upon the dominance of surface tension, allow for the planarization of the layout of the devices of the present invention which, in turn, simplifies both device fabrication and operation while also enabling high-throughput arrays in well plate-like configurations.

In view of the foregoing, it is noted that the cross-sectional area of input 52 to first channel 38 is greater than the cross-sectional area of output 62 of first channel 38. As a result, biological sample 106 flows into first channel 38 through input 52 thereof. However, the surface tension of isolation buffer 109 in second cavity 37 of second well 26 at output 62 of first channel 38 prevents biological sample 106 from flowing into second cavity 37 of second well 26 through output 62 of first channel 38. Likewise, the surface tension of reagent 113 in third cavity 78 of third well 66 at output 102 of second channel 79 prevents isolation buffer 109 from flowing into third cavity 78 of third well 66 at output 102 of second channel 79.

Figure 4:
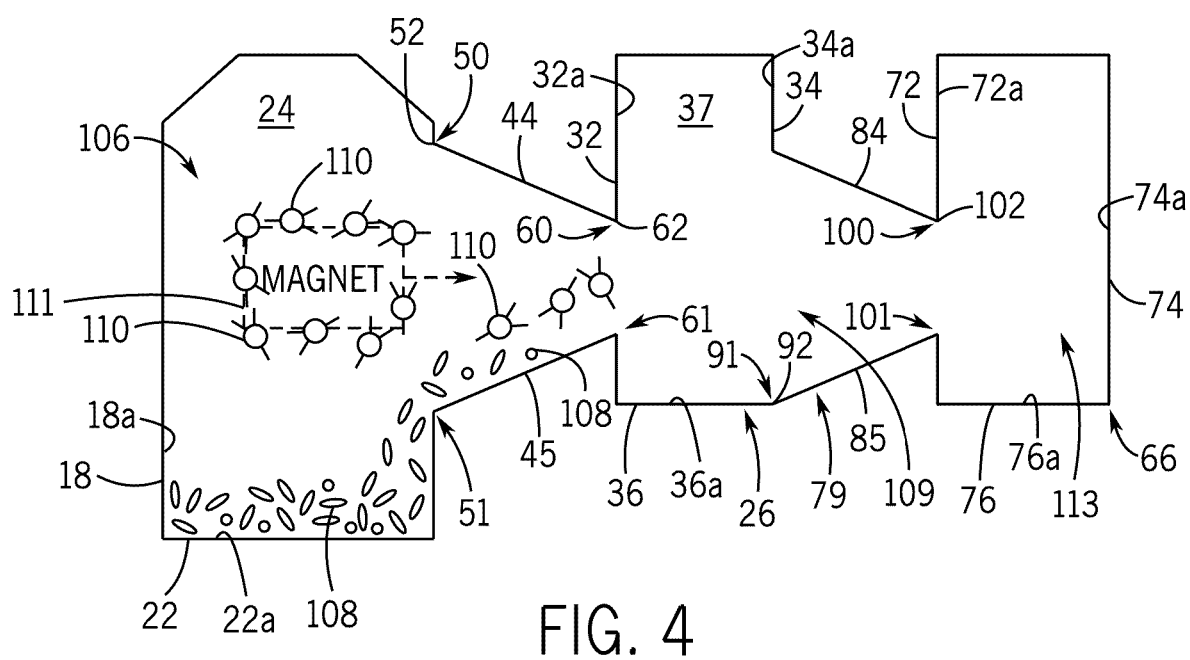
FIG. 4 is a schematic, cross-sectional view of the device, similar to FIG. 3, showing an initial step of the methodology of the present invention.

In order to extract fraction-bound solid phase substrate 110 from biological sample 106, a force to which the solid phase substrate is attracted, such as magnet 111, is positioned adjacent second sidewall 19 of device 10 at a location aligned with second sidewall 16 of input well 12 in a plane containing axis 39 of first and second channels 38 and 79, respectively, FIG. 4. As heretofore described, it is contemplated for the solid phase substrate to be a paramagnetic material attracted to a corresponding magnetic field generated by magnet 111. As such, fraction-bound solid phase substrate 110 are drawn towards axis 39 through first and second channels 38 and 79, respectively, thereby suspending fraction-bound solid phase substrate 110 above bottom wall 22 of input well 12. With fraction-bound solid phase substrate 110 suspended above bottom wall 22 of input well 12, non-desired material 108 in biological sample 106 settles passively to bottom wall 22 of input well 12 of device 10. Thereafter, magnet 111 is moved adjacent second sidewall 19 of device 10 along an axis generally parallel to axis 39. More specifically, magnet 111 moves from the location aligned with second sidewall 16 of input well 12 to a location aligned with second sidewall 42 of first channel 38 such that fraction-bound solid phase substrate 110 are drawn into first channel 38 through input 52 thereof. It can be appreciate that with fraction-bound solid phase substrate 110 suspended above bottom wall 22 of input well 12, fraction-bound solid phase substrate 110 is free to travel from input well 12 to first channel 38 without interference from non-desired material 108 in biological sample 106 that previously settled to bottom wall 22 of input well 12 of device 10, thereby allowing for a higher percentage of the fraction-bound solid phase substrate 110 to be drawn through device 10 than prior methods.

Figure 5:
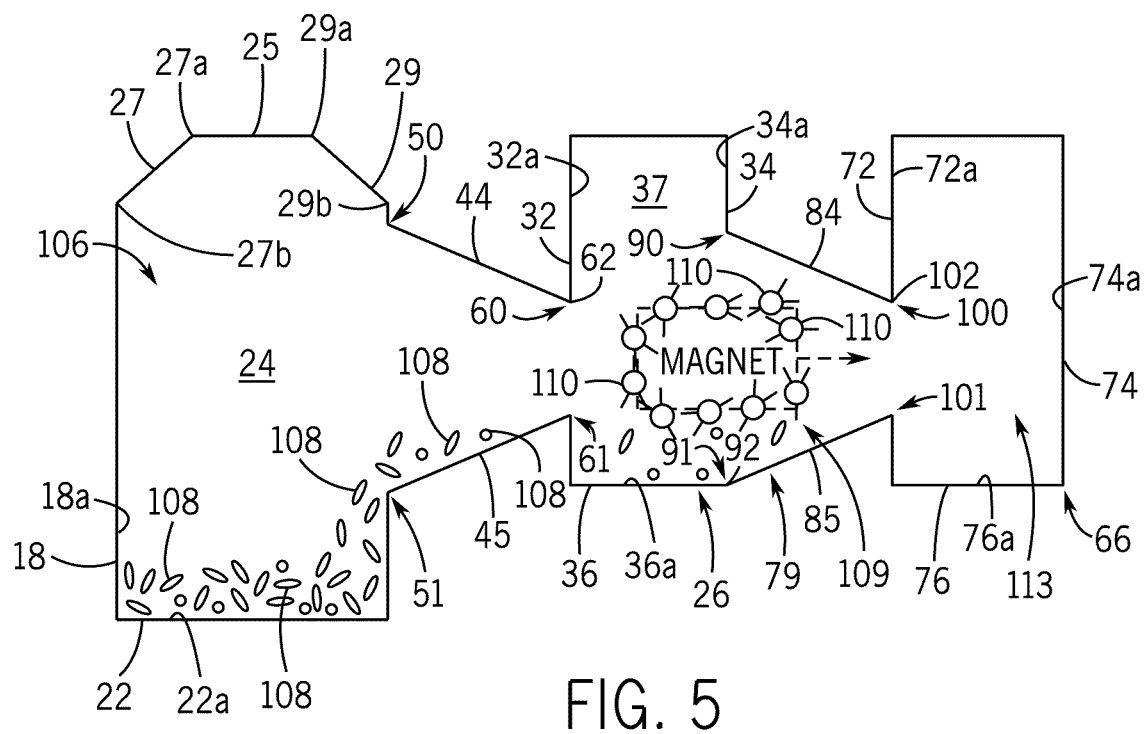
FIG. 5 is a schematic, cross-sectional view of the device, similar to FIG. 3, showing a second step of the methodology of the present invention.

Magnet 111 is then moved axially along second sidewall 19 of device 10 from the location aligned with second sidewall 42 of first channel 38 to a location aligned with second sidewall 30 of second well 26 such that fraction-bound solid phase substrate 110 is drawn along axis 39 into second well 26 through output 62 of first channel 38, FIG. 5. As fraction-bound solid phase substrate 110 is drawn into second well 26, fraction-bound solid phase substrate 110 is suspended above bottom wall 36. With fraction-bound solid phase substrate 110 suspended above bottom wall 36 of second well 26, any non-desired material 108 in biological sample 106 inadvertently drawn into second well 26 with fraction-bound solid phase substrate 110 is then allowed to settle passively to bottom wall 36 of second well 26 of device 10.

Once any non-desired material 108 in biological sample 106 inadvertently drawn into second well 26 with fraction-bound solid phase substrate 110 is allowed to settle passively to bottom wall 36 of second well 26 of device 10, magnet 111 is moved axially along second sidewall 19 of device 10 from the location aligned with second sidewall 30 of second well 26 to a location aligned with second sidewall 82 of second channel 79 such that fraction-bound solid phase substrate 110 is drawn into second channel 79 through input 92 thereof. It can be appreciate that with fraction-bound solid phase substrate 110 suspended above bottom wall 36 of second well 12, fraction-bound solid phase substrate 110 are free to travel from second well 26 to second channel 79 without interference from non-desired material 108 in biological sample 106 that previously settled to bottom wall 36 of second well 26 of device 10.

Figure 6:
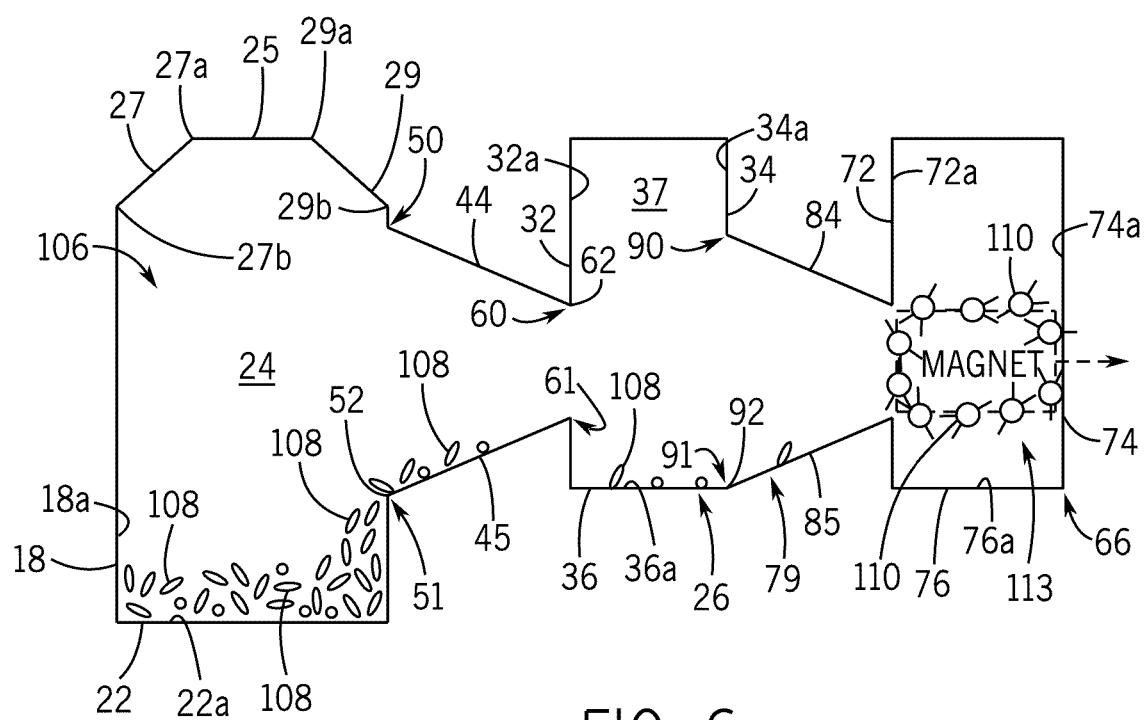
FIG. 6 is a schematic, cross-sectional view of the device, similar to FIG. 3, showing a third step of the methodology of the present invention.
Figure 7:
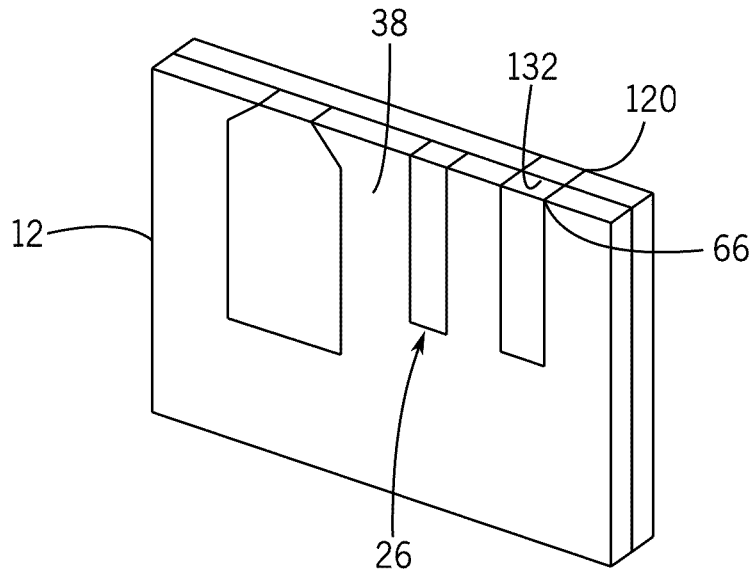
FIG. 7 is an isometric view of an alternate embodiment of the device of the present invention.
Figure 8:
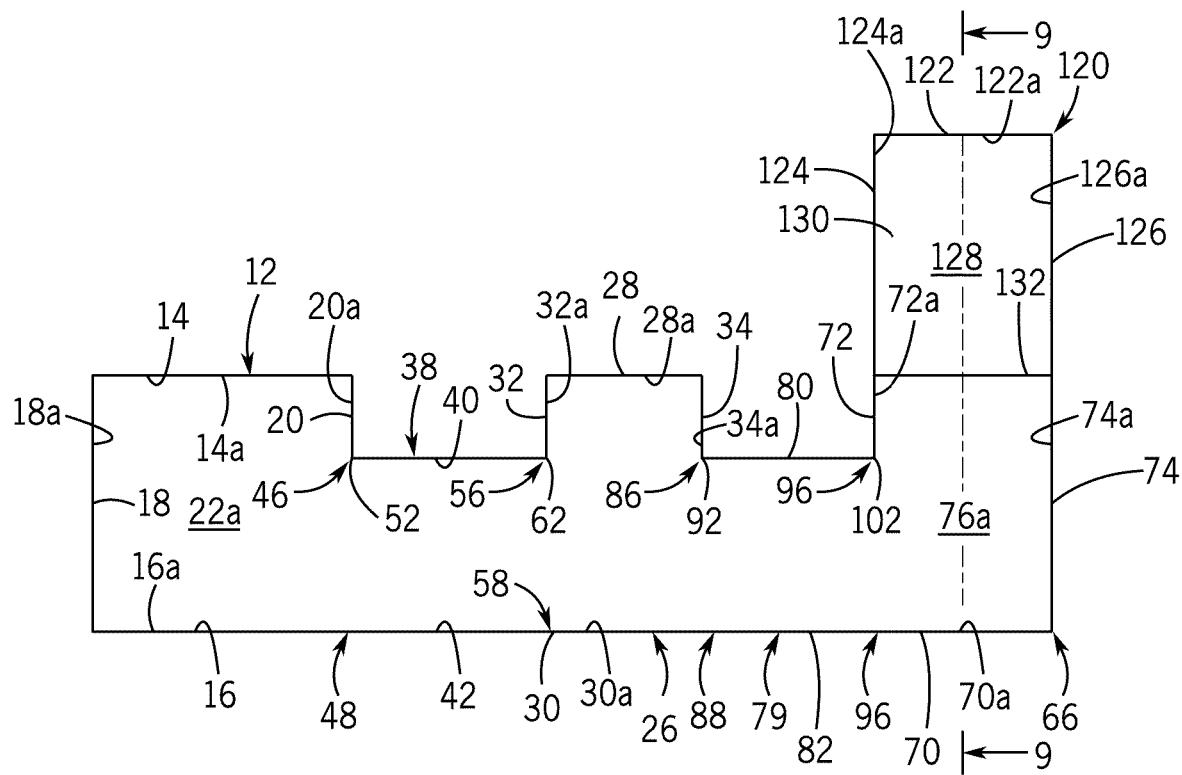
FIG. 8 is a top plan view of the device of FIG. 7
Figure 9:
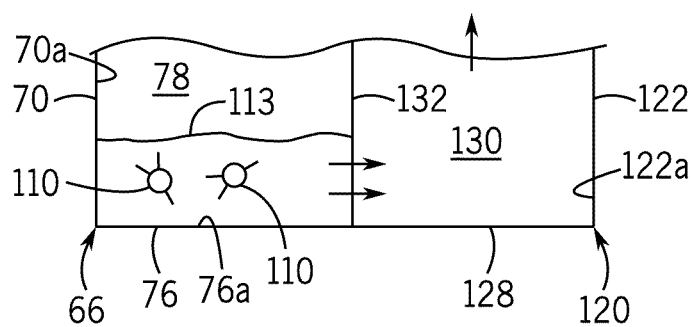
FIG. 9 is a schematic, cross-sectional view of the device taken along line 9-9 of FIG. 8 showing an additional step the methodology of the present invention.
Figure 10:
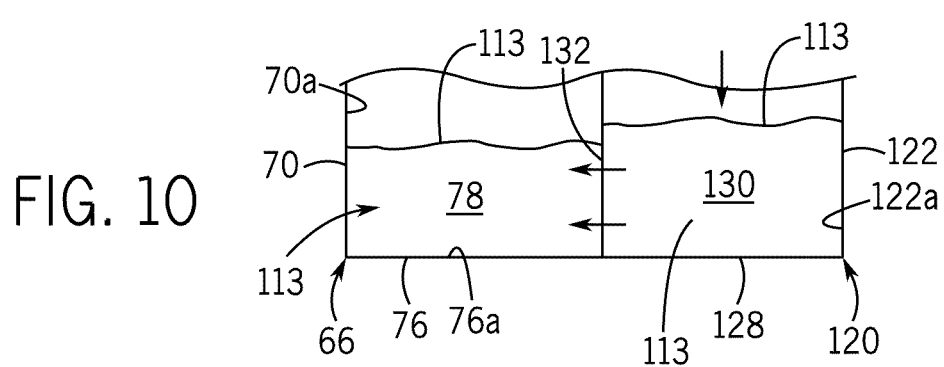
FIG. 10 is a schematic, cross-sectional view of the device, similar to FIG. 9, showing a still further step of the methodology of the present invention.

Magnet 111 is then moved axially along second sidewall 19 of device 10 from the location aligned with second sidewall 82 of second channel 79 to a location aligned with second sidewall 70 of third well 66 such that fraction-bound solid phase substrate 110 are drawn along axis 39 into third well 66 through output 102 of second channel 79, FIG. 6. As fraction-bound solid phase substrate 110 are drawn into third well 66, fraction-bound solid phase substrate 110 are suspended above bottom wall 76. With fraction-bound solid phase substrate 110 suspended above bottom wall 76 of third well 66, any non-desired material 108 in biological sample 106 inadvertently drawn into third well 66 with fraction-bound solid phase substrate 110, if any, are then allowed to settle passively to bottom wall 76 of third well 66 of device 10.

As previously noted, the surface tension of isolation buffer 109 in second cavity 37 of second well 26 at output 62 of first channel 38 prevents biological sample 106 from flowing into second cavity 37 of second well 26 through output 62 of first channel 38 and the surface tension of reagent 113 in third cavity 78 of third well 66 at output 102 of second channel 79 prevents isolation buffer 109 from flowing into third cavity 78 of third well 66 at output 102 of second channel 79. It can be appreciated that as fraction-bound solid phase substrate 110 passes through second well 26 and second channel 79, fraction-bound solid phase substrate 110 are washed by isolation buffer 109 therein, thereby effectively isolating fraction-bound solid phase substrate 110 from the remainder of biological sample 106. With fraction-bound solid phase substrate 110 isolated from the remainder of biological sample 106 in third well 66, fraction-bound solid phase substrate 110 may be treated in third well 66 by reagent 113 contained therein, as desired by a user. Alternatively, it is contemplated for reagent 113 in third well 66 to be an elution buffer such that the fraction bound to the solid phase substrate may be extracted therefrom. In addition, it can be appreciated that third well 66 may be operatively connected to additional downstream components for further processing of fraction-bound solid phase substrate 110.

As described, the methodology of the present invention does not require any electronic equipment such as centrifuges, rockers/shakers, or incubators, while consuming only minimal volumes of reagents in the three wells. It can also be appreciated that the simplicity of device 10 allows for it to be easily reconfigured to form a mating relationship with the input/output requirements of upstream and downstream components.

It is also noted that it contemplated as being within the scope of the present invention to provide an array of the devices as heretofore described in combination with an array of permanent magnets in a 1:1 ratio. Alternatively, an array of electromagnets may be utilized to provide adaptable and programmable movement of the magnetic field with no moving parts. Also, bar magnets that simultaneously move the solid phases through multiple independent wells may be used. It can be further appreciated that either the magnet 111 or the device 10 of the present invention can be the movable part to effectuate the methodology of the present invention. Additionally, it can be appreciated that physical alignment constructs ensure precise alignment between the device of the present invention and the magnetic apparatus.

Referring to FIGS. 7-10, in order to provide for the simple media replacement of reagent 113 in third cavity 78 of third well 66, it is contemplated to position replacement well 120 adjacent third well 66. More specifically, replacement well 120 is defined by first sidewall 122, first and second end walls 124 and 126, respectively, and bottom wall 128. Inner surface 122a of first sidewall 122, inner surfaces 124a and 126a of first and second end walls 124 and 126, respectively, and the upper surface of bottom wall 128 define replacement cavity 130 for receiving a replacement media therein. While replacement well 120 has a generally rectangular configuration in the depicted embodiment, other configurations are contemplated without deviating from the scope of the present invention. As described, it is intended for first and second end walls 124 and 126, respectively, and bottom wall 128 of replacement well 120 to be generally co-planar with corresponding upstream wall 72, downstream wall 74 and bottom wall 76 of third well 66, FIG. 8. Micropourous membrane 132 is positioned between replacement cavity 130 and third cavity 78 to separate the cavities.

In operation, biological sample 106 is deposited in input cavity 24 of input well 12; isolation buffer 109, such as oil or wax, is deposited in second cavity 37 of second well 26; and a desired reagent 113 is deposited in third cavity 78 of third well 66, as heretofore described. Reagent 113 is also deposited in replacement cavity 130 of replacement well 120. Thereafter, fraction-bound solid phase substrate 110 is drawn into third well 66, as heretofore described. In order to replace reagent 113 in third cavity 78 of third well 66, reagent 113 is aspirated from replacement cavity 130, FIG. 9. During aspiration, reagent 113 in third cavity 78 flows through micropourous membrane 132 and into replacement cavity 130, thereby allowing both replacement cavity 130 and third cavity 78 to be emptied. It can be appreciated that micropourous membrane 132 prevents fraction bound solid phase substrate 110 (as well as any cells, beads, analyte or the like) in third cavity 78 from flowing into replacement cavity 130 and being aspirated. This, in turn, allows for the replacement of reagent 113 in third cavity 78 without ever have to remove or centrifuge fraction-bound solid phase substrate 110 from reagent 113 in third cavity 78. Once all of reagent 113 is removed from third cavity, new media may be added to replacement cavity 130. The new media flows through micropourous membrane 132 and fills third cavity 78. These steps can be repeated multiple times, thereby allowing staining, permeabalization, fixation, etc. to take place in third cavity 78 without ever removing fraction-bound solid phase substrate 110 or the like from device 10. As a result, the loss of any fraction of interest due to the transfer of such fraction from device 10 to alternative device, e.g. a test tube, is eliminated.

Figure 11A:
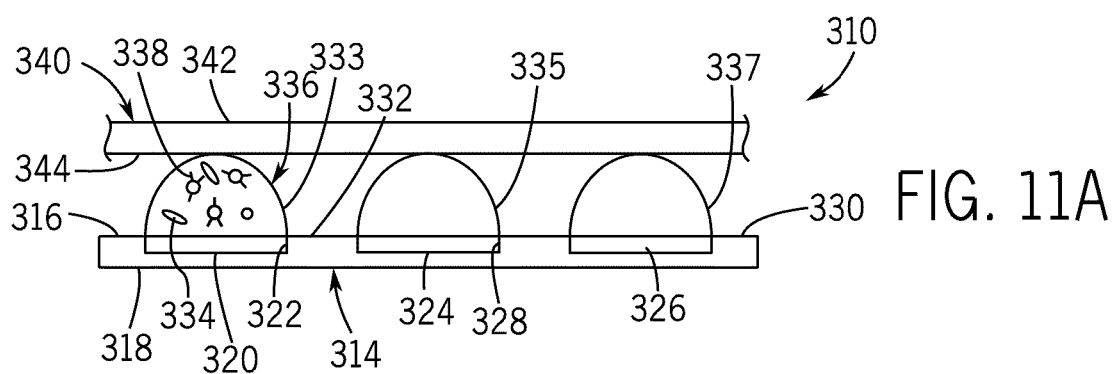
FIG. 11A is a cross-sectional view of a second embodiment of the device in accordance with the present invention in an initial configuration.
Figure 11B:
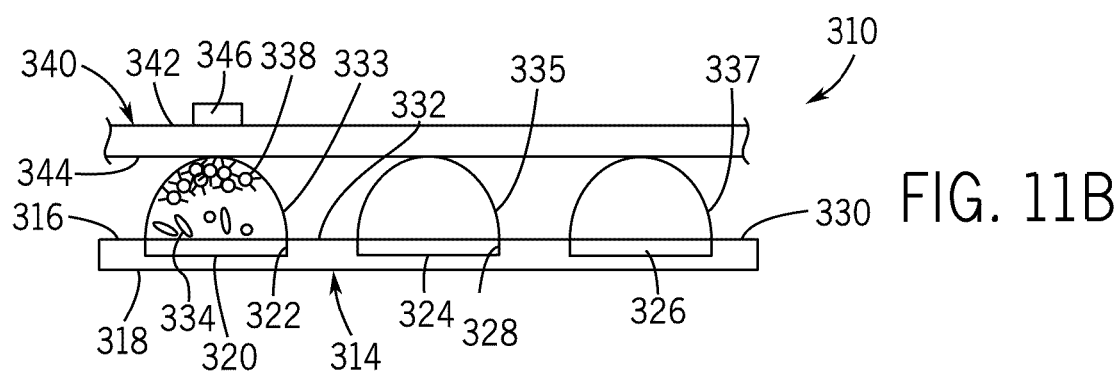
FIG. 11B is a cross-sectional view of the device of FIG. 11A in a second configuration.
Figure 11C:
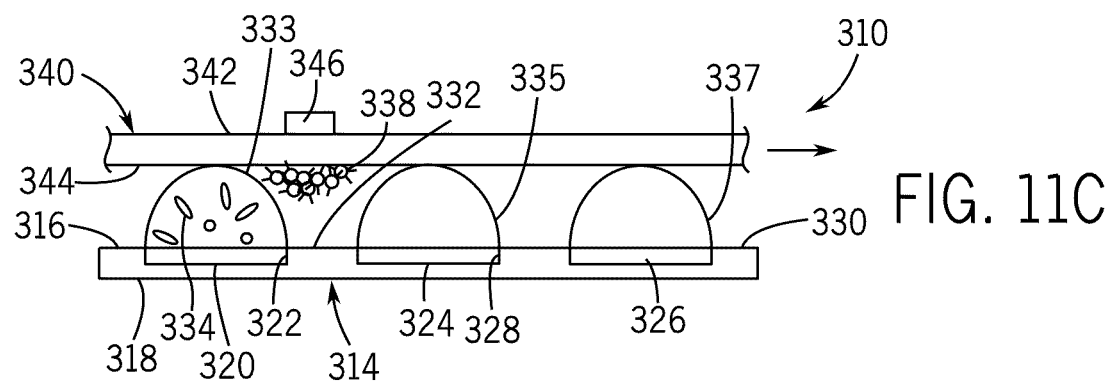
FIG. 11C is a cross-sectional view of the device of FIG. 11A in a third configuration.
Figure 11D:
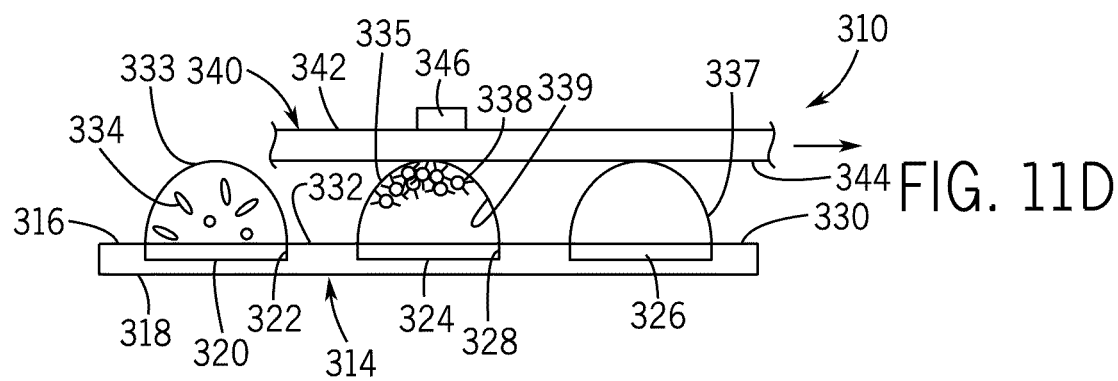
FIG. 11D is an isometric view of a device of FIG. 11A in a fourth configuration.
Figure 11E:
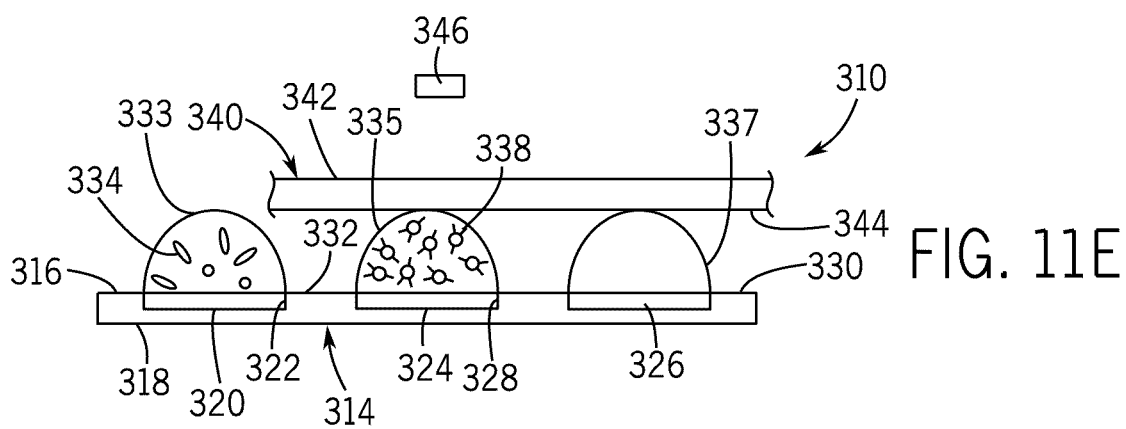
FIG. 11E is a cross-sectional view of the device of FIG. 11A in a fifth configuration.
Figure 11F:
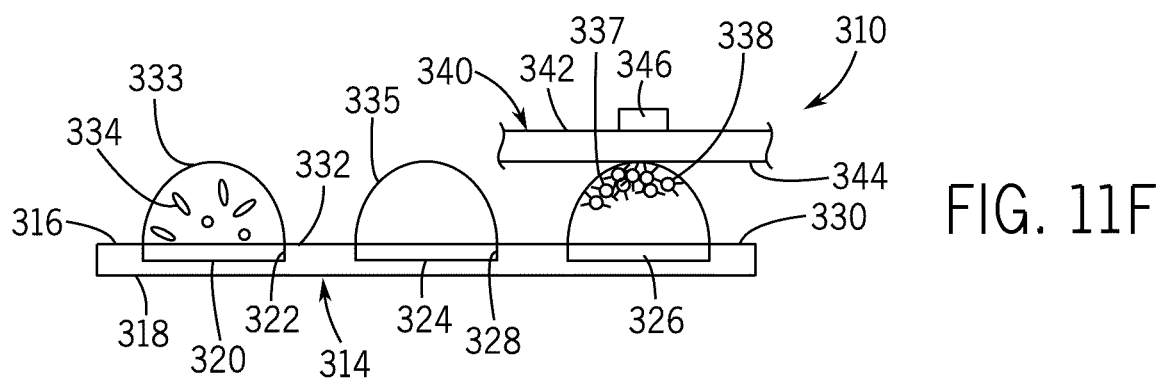
FIG. 11F is a cross-sectional view of the device of FIG. 11A in a sixth configuration.
Figure 11G:
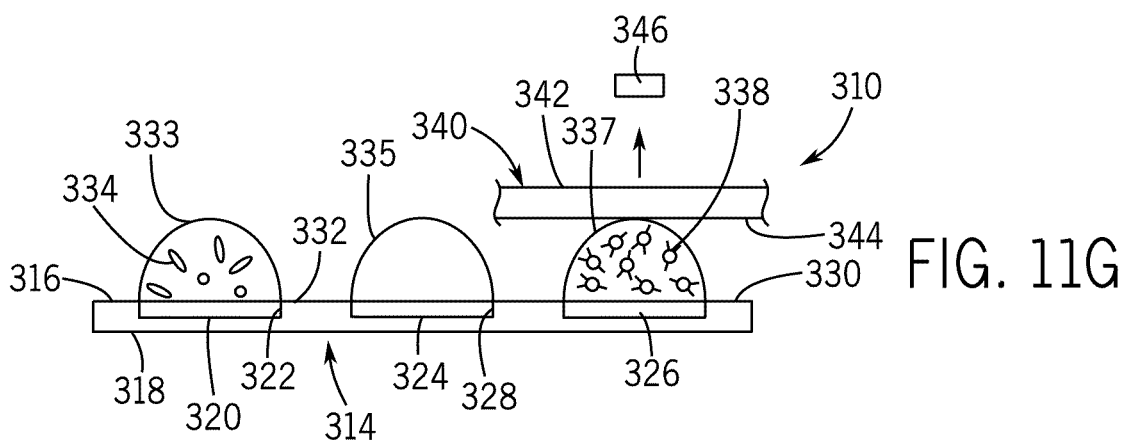
FIG. 11G is a cross-sectional view of the device of FIG. 11A in a seventh configuration.
Figure 12:
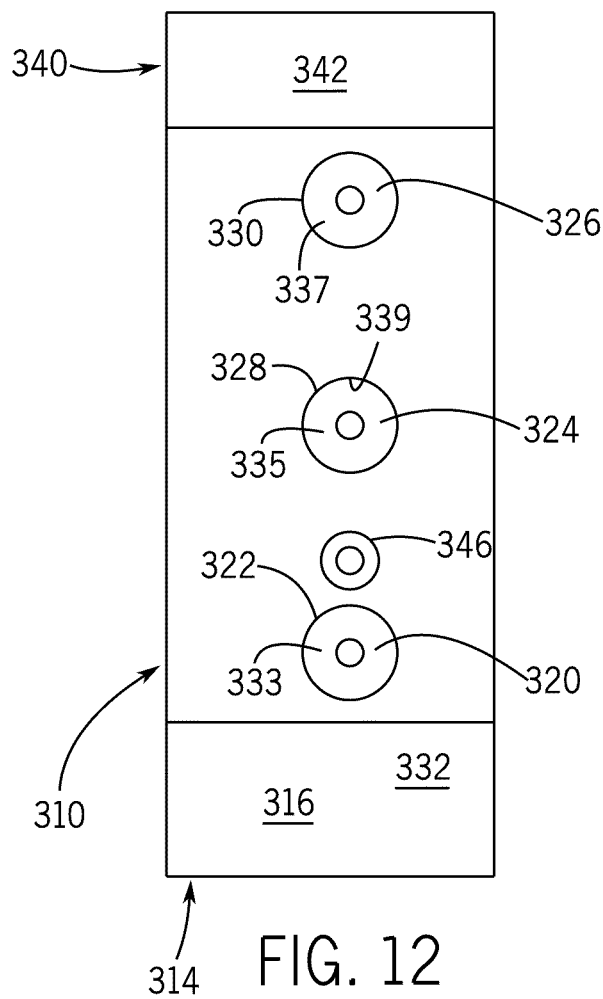
FIG. 12 is a top plan view of the device of FIG. 11A in the third configuration.
Figure 13:
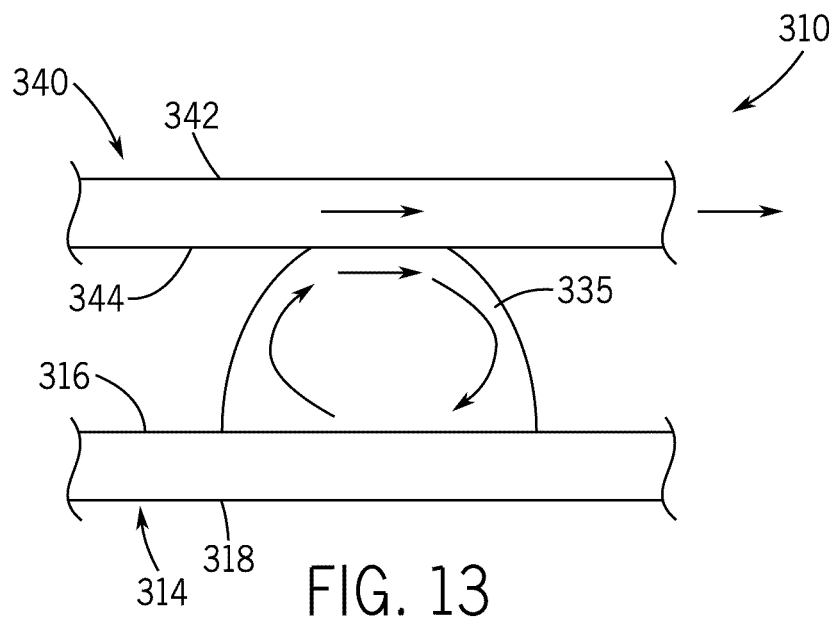
FIG. 13 is an enlarged, cross-sectional view showing a portion of the device of FIG. 11A during operation.

Referring to FIGS. 11-13, another embodiment of a device and a method for extracting and purifying a targeted fraction, such as DNA, RNA, and proteins, from complex biological samples, including cultured cells, tissue samples and other biological materials, in accordance with the present invention is generally designated by the reference numeral 310. Device 310 includes a lower first plate 314 having upper and lower surfaces 316 and 318, respectively. Except as hereinafter described, upper surface 316 of lower plate 314 is hydrophobic. Upper surface 316 of first plate 314 includes first region 320 defined by edge 322 such that first region 320 has a generally circular configuration. However, other configurations are contemplated as being within the scope of the present invention. It is intended for first region 320 to spatially retain a selected fluid thereon, as hereinafter described. By way of example, it is contemplated for first region 320 to be hydrophilic. Alternatively, it can be appreciated that first region 320 may: 1) utilize various geometric configurations; 2) take the form of a well within upper surface 316 of first plate 314; or 3) include a wall extending around the periphery thereof to spatially retain a selected fluid thereon.

Upper surface 316 of first plate 314 may further include second and third regions 324 and 326, respectively, defined by corresponding edges 328 and 330, respectively, such that second and third regions 324 and 326, respectively, have generally circular configurations. However, other configurations are contemplated as being within the scope of the present invention. It is intended for second and third regions 324 and 326, respectively, to spatially retain selected fluids thereon, as hereinafter described. By way of example, it is contemplated for second and third regions 324 and 326, respectively, to be hydrophilic. Alternatively, it can be appreciated that second and third regions 324 and 326, respectively, may: 1) utilize various geometric configurations; 2) take the form of wells within upper surface 316 of first plate 314; or 3) include walls extending around the peripheries thereof to spatially retain selected fluids thereon. Further, the portion of upper surface 316 of first plate 314 outside of first, second and third regions 320, 324 and 326, respectively, defines hydrophobic region 332.

Device 310 further includes an upper second plate 340 having upper and lower surfaces 342 and 344, respectively. Except as hereinafter described, lower surface 344 of second plate 340 is hydrophobic. Magnet 346 is supported by upper surface 342 of second plate 340. It is contemplated for magnet 346 to be axially movable between a first position wherein magnet 346 is adjacent to upper surface 342 of second plate 340 and a second position axially spaced from upper surface 342 of second plate 340, for reasons hereinafter described.

It is intended to utilize device 310 to extract a targeted fraction, such as DNA, RNA, proteins nucleic acids, whole cells and/or the like, from biological sample 336. As is known, biological sample 336 may include non-desired material 338 such as lysate, bodily fluids, forensic samples, and/or biological contaminations. In order to prepare biological sample 336 for extraction of the fraction, an appropriate reagent is added to biological sample 336 and mixed such that the fraction binds to a solid phase substrate in the reagent to form fraction-bound solid phase substrate 338. It is contemplated for the solid phase substrate to be attracted to a corresponding force. For example, the solid phase substrate may be a paramagnetic material attracted to a corresponding magnetic field. Other non-magnetic mechanisms such as gravity, optical force, ultrasonic actuation or the like are contemplated as being within the scope of the present invention.

Once mixed with the reagent, droplet 333 of biological sample 336 is deposited on first region 320 in any conventional matter such as by a micropipette or like. Alternatively, it is contemplated to provide a channel within first plate 314 having an output in communication with first region 320 so as to allow biological sample 336 to be flowed in first region 320. In addition, droplet 335 of a first reagent (e.g. wash, secondary antibody, etc.) is deposited on second region 324 and droplet 337 of a second reagent is deposited on third region 326. It is contemplated for the volumes of droplets 333, 335 and 337 to be generally equal. It can be appreciated that the hydrophillic nature of first, second and third regions 320, 324 and 326, respectively, act to pin droplets 333, 335 and 337 thereon. In addition, the hydrophobic region 332 of upper surface 316 of first plate 314 further acts to retain droplets 333, 335 and 337 on first, second and third regions 320, 324 and 326, respectively.

After depositing droplets 333, 335 and 337 on first, second and third regions 320, 324 and 326, respectively, second plate 340 is positioned such that lower surface 344 thereof is in close proximity to or makes contact with droplets 333, 335 and 337 and such that magnet 346 is axially aligned with first region 320 of upper surface 316 of first plate 314, FIG. 11A, Lower surface 344 of second plate 340 is maintained a predetermined distance from upper surface 316 of first plate 314 such that droplets 333, 335 and 337 maintain their generally cylindrical shapes and are not squashed.

With second plate 340 positioned, as heretofore described, magnet 346 is positioned adjacent upper surface 342 of second plate 340 and magnetically attracts fraction-bound solid phase substrate 338 such that fraction-bound solid phase substrate 338 are drawn toward lower surface 344 of second plate 340, FIG. 11B. Any undesired (or unbound) material in droplet 333 is free to drop towards upper surface 316 of first plate 314. Thereafter, with first plate 314 remaining stationary, second plate 340 is moved axially in a first direction, FIG. 11C. The hydrophobic nature of lower surface 344 of second plate 340 prevents second plate 340 from adhereing to droplets 333, 335 and 337, thereby insuring that droplets 333, 335 and 337 maintain their integrity as second plate 340 is axially moved. As second plate 340 is moved, magnet 346 retains fraction-bound solid phase substrate 338 against lower surface 344 of second plate 340, thereby allowing fraction-bound solid phase substrate 338 to break the surface tension of droplet 333 when fraction-bound solid phase substrate 338 reach the outer periphery thereof. Second plate 40 continues to be moved in the first direction such that magnet 346 is axially aligned with second region 324 of upper surface 316 of first plate 314, FIG. 11D. Fraction-bound solid phase substrate 338 may be deposited in droplet 335 on second region 324 simply by moving magnet 346 axially away from upper surface 342 of second plate 340, FIG. 11E, thereby freeing fraction-bound solid phase substrate 338 from the magnetic force thereof. To assure that all of fraction-bound solid phase substrate 338 are retained in droplet 335, first plate 314, and hence magnet 346, is slid past droplet 335 prior to axially moving magnet 346 away from upper surface 342 of second plate 340. More specifically, the movement of first plate 314 and second plate 340 with respect to each other causes Couette flow within droplet 335 such that droplet 335 mixes within itself, FIG. 13. In addition, the surface tension of posterior end 339 of droplet 335 pulls fraction-bound solid phase substrate 338 off hydrophobic, lower surface 344 of second plate 340.

In order to move fraction-bound solid phase substrate 338 into droplet 337, magnet 346 is repositioned adjacent of upper surface 342 of second plate 340 in axial alignment with second region 324 of upper surface 316 of first plate 314. With magnet 346 repositioned, as heretofore described, magnet 346 magnetically attracts fraction-bound solid phase substrate 338 such that fraction-bound solid phase substrate 338 are drawn toward lower surface 344 of second plate 340, FIG. 11D. With first plate 314 remaining stationary, second plate 340 is moved axially in the first direction. As second plate 340 is moved, magnet 346 retains fraction-bound solid phase substrate 338 against lower surface 344 of second plate 340, thereby allowing fraction-bound solid phase substrate 338 to break the surface tension of droplet 335 when fraction-bound solid phase substrate 338 reach the outer periphery thereof. Second plate 340 continues to be moved in the first direction such that magnet 346 is axially aligned with third region 326 of upper surface 316 of first plate 314, FIG. 11F. With magnet 346 is axially aligned with third region 326 of upper surface 316 of first plate 314, magnet 346 is moved axially away from upper surface 342 of second plate 340, FIG. 11G, thereby freeing fraction-bound solid phase substrate 338 within droplet 337 on third region 326. As described, fraction-bound solid phase substrate 338 is then allowed to passively mix into droplet 337. To assure that all of fraction-bound solid phase substrate 338 beads are retained in droplet 337, first plate 314, and hence magnet 346, is slid past droplet 337 prior to axially moving magnet 346 away from upper surface 342 of second plate 340. More specifically, the movement of first plate 314 and second plate 340 with respect to each other causes Couette flow within droplet 337 such that droplet 337 mixes within itself. In addition, the surface tension of the posterior end of droplet 337 pulls fraction-bound solid phase substrate 338 off hydrophobic, lower surface 344 of second plate 340.

It can be appreciated that the above description of device 310 is merely exemplary of the present invention. Various modifications to device 310 are possible without deviating from the scope of the present invention. By way of example, it is contemplated for first plate 314 to be axially moveable with respect to second plate 340, such movement of first plate 314 (or a combination of movement of first and second plates 314 and 340, respectively) results in the droplets 333, 335 and 337 aligning with magnet 436, for reasons heretofore described. It is further contemplated to provide additional (or fewer) hydrophilic regions on upper surface 316 of first plate 314 so as to allow a user to effectuate additional (or fewer) processing steps on fraction-bound solid phase substrate 338, e.g. additional washings of fraction-bound solid phase substrate 338. Further, upper surface 316 of first plate 314 may include an array of hydrophilic regions and a corresponding array of magnets may be supported on second plate 340. As a result, a plurality of extraction operations in accordance with the methodology of the present invention may be simultaneously conducted utilizing a single device 310. In such an arrangement, it is contemplated to provided a wall or fence about each "set" of hydrophilic regions so as to effectively isolate each "set" of hydrophilic regions from the other sets in the array, thereby preventing potential cross contamination between the sets. In an alternate embodiment, it is contemplated to permanently affix magnet 346 to second plate 340. As such, instead of axially moving magnet 346 away from upper surface 342 of second plate 340 to release fraction-bound solid phase substrate 338 into a corresponding droplet, second plate 340 may be simply removed from contact with the droplets. With second plate 340 disengaged from the droplets, fraction-bound solid phase substrate 338 is allowed to passively mix in the desired droplet. It is noted that since lower surface 344 of second plate 340 is hydrophobic, the droplets do not adhere thereto thereby allowing the droplets to maintain their integrity.

Referring to FIGS. 14-17, an alternate embodiment of a device in accordance with the present invention is generally designated by the reference numeral 360. Device 360 includes lower first plate 372 having upper and lower surfaces 374 and 376, respectively. First plate 372 has a center, a diameter and a generally circular configuration defined by outer edge 378. Support 379 extends axially away from center of first plate 372 for rotationally supporting second plate 104 thereon. Except as hereinafter described, upper surface 374 of first plate 372 is hydrophobic. Upper surface 374 of first plate 372 includes a first region 380 defined by edge 382 such that first region 380 has a generally circular configuration. The center of first region 380 is a predetermined radial distance from center 388 of first plate 372. It is intended for first region 380 to spatially retain a selected fluid thereon, as hereinafter described. By way of example, it is contemplated for first region 380 to be hydrophilic. Alternatively, it can be appreciated that first region 380 may: 1) utilize various geometric configurations; 2) take the form of a well within upper surface 374 of first plate 372; or 3) include a wall extending around the periphery thereof to spatially retain a selected fluid thereon.

Upper surface 374 of first plate 372 may further include second and third regions 390 and 392, respectively, defined by corresponding edges 394 and 396, respectively, such that second and third regions 390 and 392, respectively, have generally circular configurations. The centers of second and third regions 390 and 392, respectively, are spaced from center 388 of first plate 372 by the predetermined radial distance. It is intended for second and third regions 390 and 392, respectively, to spatially retain selected fluids thereon, as hereinafter described. By way of example, it is contemplated for second and third regions 390 and 392, respectively, to be hydrophilic. Alternatively, it can be appreciated that second and third regions 390 and 392, respectively, may: 1) utilize various geometric configurations; 2) take the form of wells within upper surface 374 of first plate 372; or 3) include walls extending around the peripheries thereof to spatially retain selected fluids thereon. The portion of upper surface 74 of first plate 372 outside of first, second and third regions 380, 390 and 392, respectively, defines hydrophobic region 402.

Second plate 404 has a center, a diameter generally equal to the diameter of first plate 372, and upper and lower surfaces 406 and 408, respectively. Upper second plate 404 is rotatably supported by support 379 in spaced relation to first plate 372 such that the center of second plate 404 is axially aligned with the center of first plate 372. Lower surface 408 of second plate 404 is hydrophobic. Magnet 410 is supported by upper surface 406 of second plate 404 at a location radially spaced from the center of second plate by the predetermined radial distance. Magnet 410 is axially movable between a first position wherein magnet 410 is adjacent to upper surface 406 of second plate 404 and a second position axially spaced from upper surface 406 of second plate 404, for reasons hereinafter described.

Figure 14:
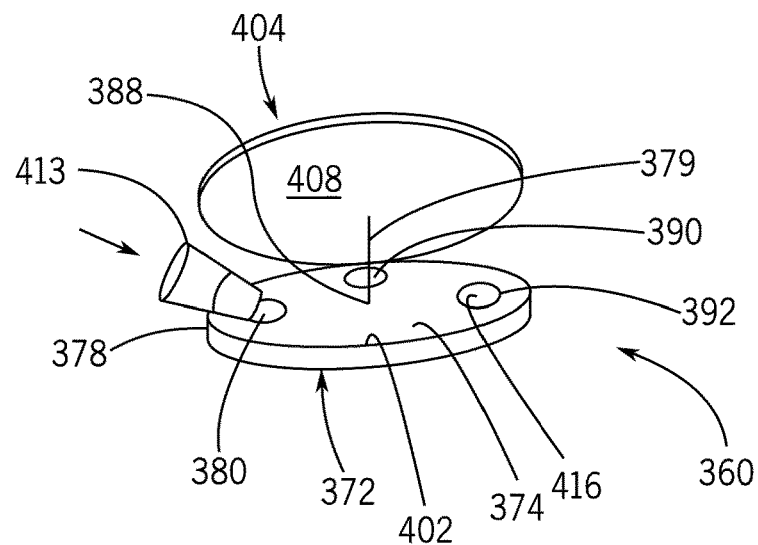
FIG. 14 is an isometric view of a third embodiment of a device in accordance with the present invention in an initial configuration.
Figure 15:
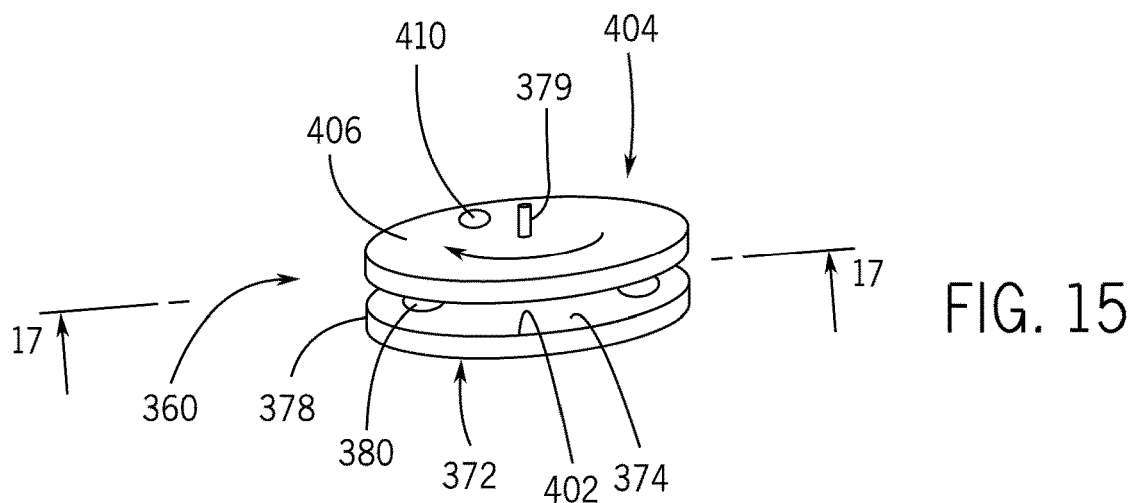
FIG. 15 is an isometric view of the device of FIG. 14 in second configuration.
Figure 16:
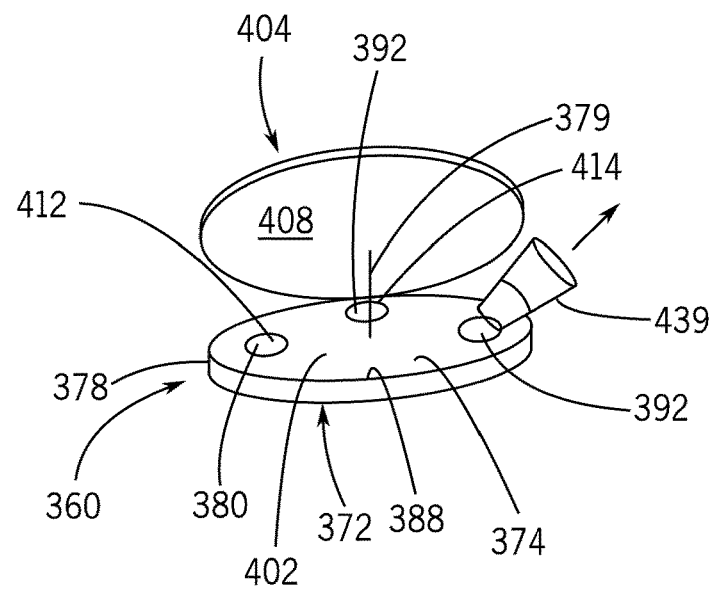
FIG. 16 is an isometric view of the device of FIG. 14 in third configuration.
Figure 17:
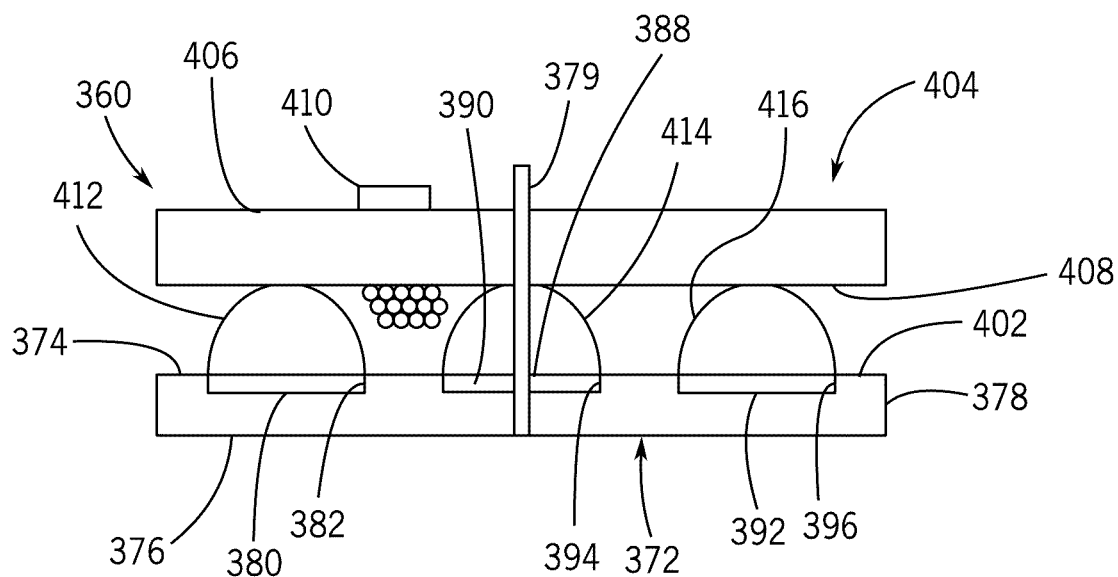
FIG. 17 is a cross-sectional view of the device of FIG. 15 taken along line 17-17.

In order to extract the targeted fraction from biological sample 336, droplet 412 of biological sample 336 is deposited on first region 380 in any conventional matter such as by a micropipette 413 or like, FIG. 14. Alternatively, it is contemplated to provide a channel within first plate 372 having an output in communication with first region 380 so as to allow biological sample 336 to be flowed in first region 380. In addition, droplet 414 of a first reagent (e.g. wash, secondary antibody, etc.) is deposited on second region 390 and droplet 416 of a second reagent is deposited on third region 392. It is contemplated for the volumes of droplets 412, 414 and 416 to be generally equal. Second plate 404 is positioned such that lower surface 408 thereof is in close proximity to or makes contact with droplets 412, 414 and 416 and such that magnet 410 is axially aligned with first region 380 of upper surface 374 of first plate 372. Lower surface 408 of second plate 404 is maintained a predetermined distance from upper surface 374 of first plate 372 by support 379 such that droplets 412, 414 and 416 maintain their generally cylindrical shapes and are not squashed.

With second plate 404 positioned as heretofore described, magnet 410 magnetically attracts fraction-bound solid phase substrate 338 such that fraction-bound solid phase substrate 338 are drawn toward lower surface 408 of second plate 404. With first plate 372 remaining stationary, second plate 404 is rotated axially in a first direction, FIGS. 15 and 17. As second plate 404 is moved, magnet 410 retains fraction-bound solid phase substrate 338 against lower surface 408 of second plate 404, thereby allowing fraction-bound solid phase substrate 338 to break the surface tension of droplet 412 when fraction-bound solid phase substrate 338 reach the outer periphery thereof. Second plate 104 continues to be moved in the first direction such that magnet 410 is axially aligned with second region 390 of upper surface 374 of first plate 372. Fraction-bound solid phase substrate 338 may be deposited in droplet 414 on second region 390 simply by moving magnet 410 axially away from upper surface 374 of second plate 404. To assure that all of fraction-bound solid phase substrate 338 are retained in droplet 414, second plate 404, and hence magnet 410, is slid past droplet 414 prior to axially moving magnet 410 away from upper surface 406 of second plate 404, More specifically, the movement of first plate 372 and second plate 404 with respect to each other causes Couette flow within droplet 414 such that droplet 414 mixes within itself. In addition, the surface tension of the posterior end of droplet 414 pulls fraction-bound solid phase substrate 338 off hydrophobic, lower surface 408 of second plate 404.

In order to move fraction-bound solid phase substrate 338 into droplet 416, magnet 410 is repositioned adjacent of upper surface 406 of second plate 404 in axial alignment with second region 390 of upper surface 374 of first plate 372. With magnet 410 repositioned, as heretofore described, magnet 410 magnetically attracts fraction-bound solid phase substrate 338 such that fraction-bound solid phase substrate 338 are drawn toward lower surface 408 of second plate 404. With first plate 372 remaining stationary, second plate 404 is rotated in the first direction. As second plate 404 is moved, magnet 410 retains fraction-bound solid phase substrate 338 against lower surface 408 of second plate 404, thereby allowing fraction-bound solid phase substrate 338 to break the surface tension of droplet 414 when fraction-bound solid phase substrate 338 reach the outer periphery thereof. Second plate 404 continues to be rotated in the first direction such that magnet 410 is axially aligned with third region 392 of upper surface 374 of first plate 372. With magnet 410 is axially aligned with third region 392 of upper surface 406 of first plate 404, magnet 410 is moved axially away from upper surface 406 of second plate 404, thereby depositing fraction-bound solid phase substrate 338 in droplet 416 on third region 392. As described, fraction-bound solid phase substrate 338 is then allowed to passively mix into droplet 416. Droplet 416 may be removed, such as by micropipette 439, FIG. 16, for further processing.

It can be appreciated that the above description of device 360 is merely exemplary of the present invention, Various modifications to device 360 are possible without deviating from the scope of the present invention, By way of example, it is contemplated for first plate 372 to be moveable with respect to second plate 404, such movement of first plate 372 (or a combination of movement of first and second plates 372 and 404, respectively) results in the droplets 412, 414 and 416 aligning with magnet 346, for reasons heretofore described. It is further contemplated to provide additional (or fewer) hydrophilic regions on upper surface 374 of first plate 372 so as to allow a user to effectuate additional (or fewer) processing steps on fraction-bound solid phase substrate 338, e.g. additional washings of fraction-bound solid phase substrate 338. Further, upper surface 374 of first plate 372 may include an array of hydrophilic regions circumferentially spaced thereon and a corresponding array of magnets supported second plate 404. As a result, a plurality of extraction operations in accordance with the methodology of the present invention may be simultaneously conducted utilizing a single device 360. In such an arrangement, it is contemplated to provide a wall or fence about each "set" of hydrophilic regions so as to effectively isolate each "set" of hydrophilic regions from the other sets in the array, thereby preventing potential cross contamination between the sets. In an alternate embodiment, it is contemplated to permanently affix magnet 410 to second plate 404, As such, instead of axially moving magnet 410 away from upper surface 406 of second plate 404 to release fraction-bound solid phase substrate 338 into a corresponding droplet, second plate 404 is simply removed from contact with the droplets. With second plate 404 disengaged from the droplets, fraction-bound solid phase substrate 338 is allowed to passively mix into the desired droplet. It is noted that since lower surface 408 of second plate 404 is hydrophobic, the droplets do not adhere thereto thereby allowing the droplets to maintain their integrity.

Figure 18:
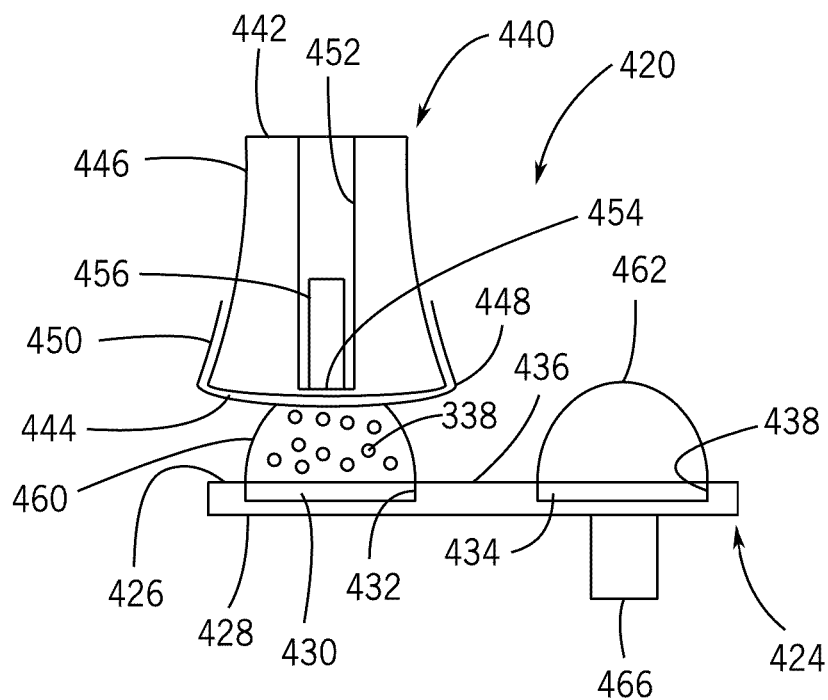
FIG. 18 is a cross-sectional view of a fourth embodiment of a device in accordance with the present invention in an initial configuration.
Figure 19:
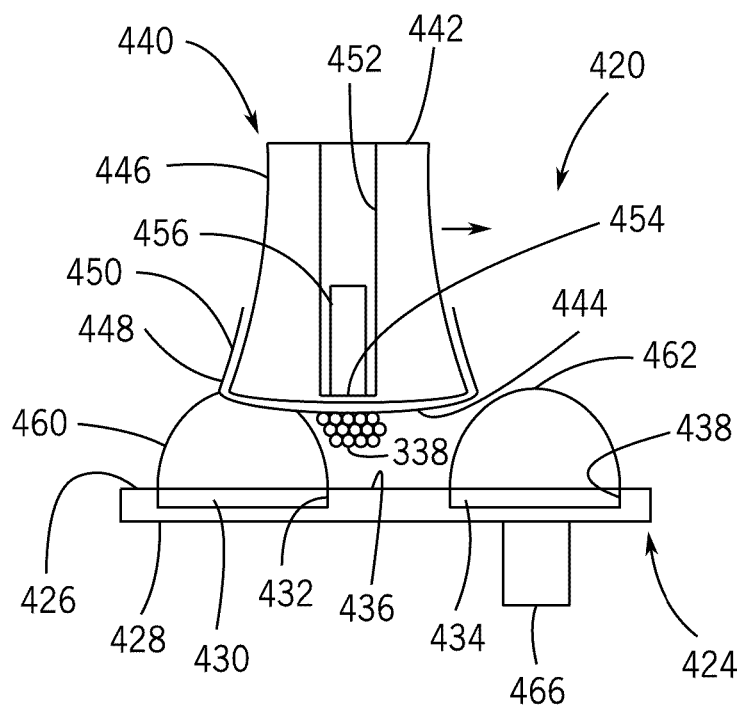
FIG. 19 is a cross-sectional view of the device of FIG. 18 in accordance with the present invention in a second configuration.
Figure 20:
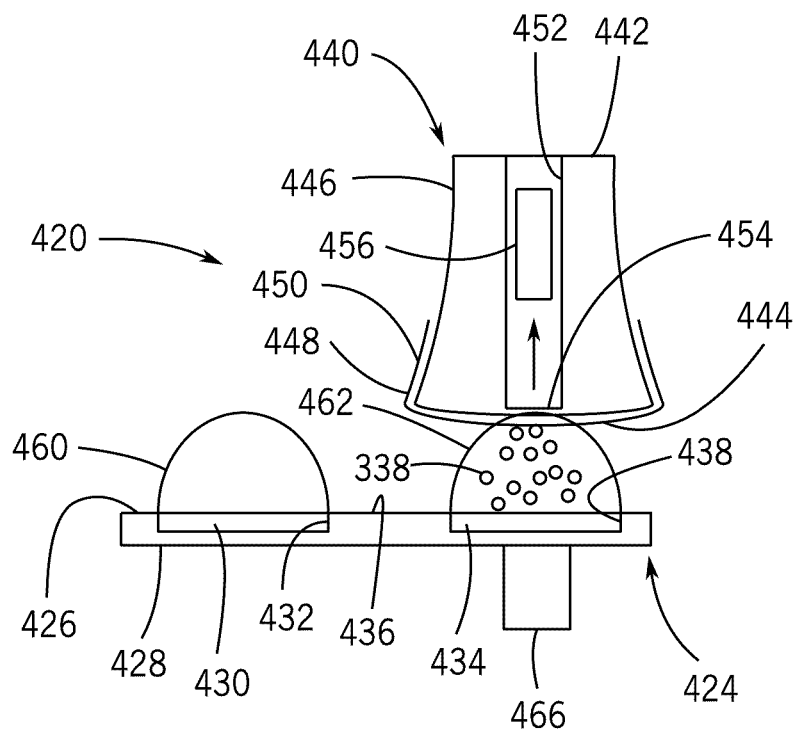
FIG. 20 is a cross-sectional view of the device of FIG. 18 in accordance with the present invention in a third configuration.

Referring to FIGS. 18-20, a still further embodiment of a device in accordance with the present invention is generally designated by the reference number 420. Device 420 includes a lower first plate 424 having upper and lower surfaces 426 and 428, respectively. Except as hereinafter described, upper surface 426 of lower plate 424 is hydrophobic. Upper surface 426 of first plate 424 includes first region 430 defined by edge 432 such that first region 430 has a generally circular configuration. However, other configurations are contemplated as being within the scope of the present invention. It is intended for first region 430 to spatially retain a selected fluid thereon, as hereinafter described. By way of example, it is contemplated for first region 430 to be hydrophilic. Alternatively, it can be appreciated that first region 430 may: 1) utilize various geometric configurations; 2) take the form of a well within upper surface 426 of first plate 424; or 3) include a wall extending around the periphery thereof to spatially retain the selected fluid thereon.

Upper surface 426 of first plate 424 may further include second region 434 defined by corresponding edge 438 such that second region 434 has a generally circular configuration. However, other configurations are contemplated as being within the scope of the present invention. It is intended for second region 434 to spatially retain a selected fluid thereon, as hereinafter described. By way of example, it is contemplated for second region 434 to be hydrophilic. Alternatively, it can be appreciated that second region 434 may: 1) utilize various geometric configurations; 2) take the form of a well within upper surface 426 of first plate 424; or 3) include a wall extending around the periphery thereof to spatially retain the selected fluid thereon. For the reasons heretofore described, additional hydrophilic regions may be provided on upper surface 426 of first plate 424, without deviating from the scope of the present invention. The portion of upper surface 426 of first plate 424 outside of first and second regions 430 and 434, respectively, defines hydrophobic region 436.

Device 420 further includes an upper plate or slide 440 extending along a longitudinal axis generally perpendicular to upper surface 426 of first plate 424 and being defined by an upper surface 442, a generally convex lower surface 444 and an outer surface 446 therebetween. Outer surface 446 of slide 440 intersects lower surface 444 of slide 440 at generally circular edge 448. It can be appreciated that edge 448 can have other configurations without deviating from the scope of the present invention. Slide 440 further include hydrophobic tape 450 covering the entirety of lower surface 444 thereof and overlapping edge 448. Tape 450 renders lower surface 444 of slide 440 hydrophobic, for reasons hereinafter described, Slide 440 further includes a magnet receiving passageway 452 extending along the longitudinal axis of slide 440 from upper surface 442 towards lower surface 444. Passageway 452 terminates at end surface 454 which is in close proximity to lower surface 444 of slide 440. Passageway 452 is adapted for slidably receiving magnet 456 therein. It is intended for magnet 456 to be axially movable between a first position wherein magnet 456 is adjacent end surface 454 and a second position axially spaced from end surface 452, for reasons hereinafter described. Magnet 456 may be moved with passageway 452 between the first and second positions in any conventional manner such as by mechanical means, a vacuum, a magnetic force or the like.

In order to extract the targeted fraction from biological sample 336, droplet 460 of biological sample 336 is deposited on first region 430 in any conventional matter such as by a micropipette or like. In addition, droplet 462 of a desired reagent is deposited on second region 434. It is contemplated for the volumes of droplets 460 and 462 to be generally equal. Slide 440 is positioned such that tape 450 on lower surface 444 thereof is in close proximity to or makes contact with droplets 460 and 462 and such that magnet 456, in its first position, is axially aligned with first region 430 of upper surface 426 of first plate 424. Lower surface 444 of slide 440, and hence tape 450, is maintained a predetermined distance from upper surface 126 of first plate 124 such that droplets 160 and 462 maintain their generally cylindrical shapes and are not squashed, FIG. 18.

With slide 440 positioned as heretofore described, magnet 456 magnetically attracts fraction bound solid phase substrate 338 such that fraction-bound solid phase substrate 338 are drawn toward lower surface 444 of slide 440. With first plate 424 remaining stationary, slide 440 is moved axially in a first direction, FIG. 19. As slide 440 is moved, magnet 456 retains fraction-bound solid phase substrate 338 against tape 450, and hence lower surface 444 of slide 440, thereby allowing fraction bound solid phase substrate 38 to break the surface tension of droplet 460 when fraction-bound solid phase substrate 38 reach the outer periphery thereof. Slide 440 continues to be moved in the first direction such that magnet 456 is axially aligned with second region 434 of upper surface 426 of first plate 424, FIG. 20. Fraction-bound solid phase substrate 338 may be deposited in droplet 462 on second region 434 simply by moving magnet 456 axially away from end surface 454 toward upper surface 442 of slide 440. To assure that all of fraction-bound solid phase substrate 338 are retained in droplet 462, slide 440, and hence magnet 456, may be slid axially past droplet 462 prior to axially moving magnet 456 away from end surface 454. More specifically, the movement of first plate 424 and slide with respect to each other causes Couette flow within droplet 462 such that droplet 462 mixes within itself. In addition, the surface tension of the posterior end of droplet 462 pulls fraction-bound solid phase substrate 338 off hydrophobic tape 450 on lower surface 444 of slide 440.

It is further contemplated to provide a second magnet 466 orientated with the opposite polarity as magnet 456 at a location below second region 434 adjacent lower surface 428 of first plate 424. As such, upon release of fraction-bound solid phase substrate 338 into droplet 462, heretofore described, fraction-bound solid phase substrate 38 will have a strong affinity to second magnet 466. This, in turn, causes fraction-bound solid phase substrate 338 to switch polarity. As the magnetic force of second magnet 466 acts to attract fraction-bound solid phase substrate 38 toward upper surface 426 of first plate 424, magnet 456 acts as a repulsive force of opposite polarity thereby urging fraction-bound solid phase substrate 38 away from lower surface 444 of slide 440

It can be appreciated that the above description of device 420 is merely exemplary of the present invention. Various modifications to device 420 are possible without deviating from the scope of the present invention. By way of example, it is contemplated for first plate 424 to be axially moveable with respect to slide 440, such movement of first plate 424 (or a combination of movement of first plate 424 and slide 440) results in the droplets 460 and 462 aligning with magnet 456, for reasons heretofore described. It is further contemplated to provide additional (or fewer) hydrophilic regions on upper surface 426 of first plate 424 so as to allow a user to effectuate additional (or fewer) processing steps on fraction-bound solid phase substrate 338, e.g. additional washings of fraction-bound solid phase substrate 338. Further, upper surface 426 of first plate 424 may include an array of hydrophilic regions circumferentially spaced thereon and a corresponding array of slides 440. As a result, a plurality of extraction operations in accordance with the methodology of the present invention may be simultaneously conducted utilizing a single device 420. In such an arrangement, it is contemplated to provided a wall or fence about each "set" of hydrophilic regions so as to effectively isolate each "set" of hydrophilic regions from the other sets in the array, thereby preventing potential cross contamination between the sets.

Figure 21:
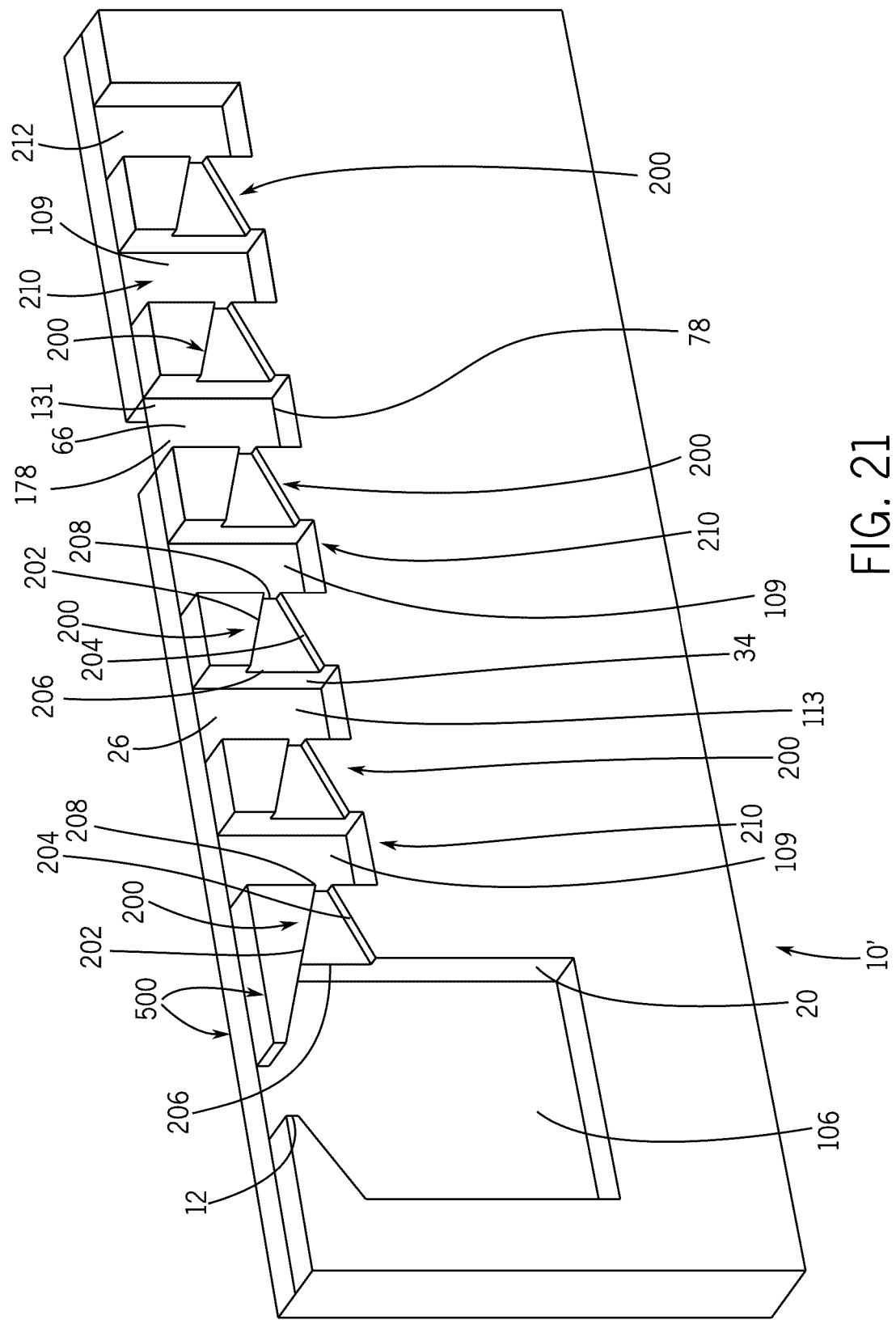
FIG. 21 is an isometric view of a fifth embodiment of the device in accordance with the present invention
Figure 22:
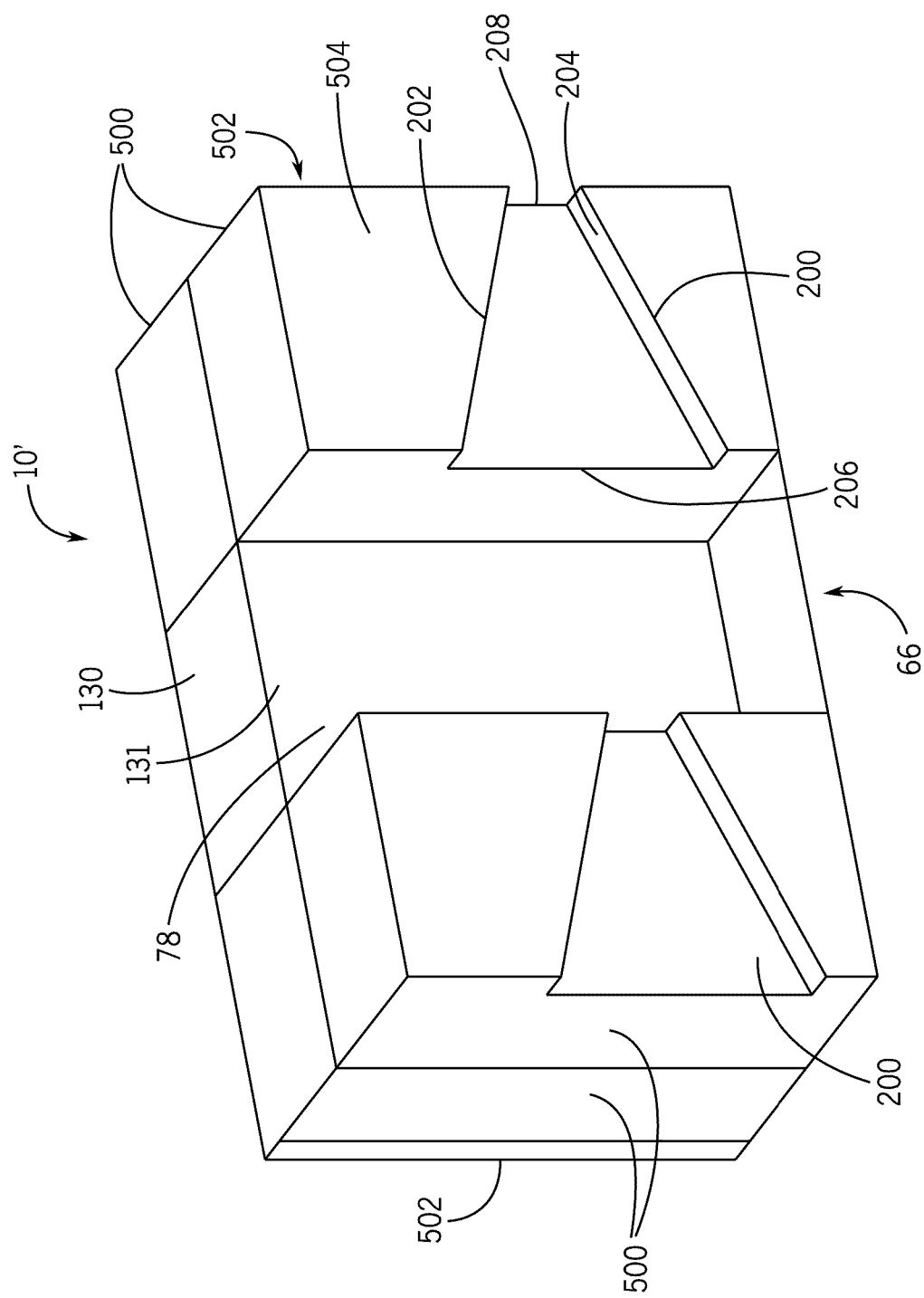
FIG. 22 is an isometric view of a sieve well of the device of FIG. 21.

Looking now at FIGS. 21 and 22 a modification of the embodiment of the device 10 of FIG. 1 is illustrated. In this embodiment, the device 10' is formed of a pair of pieces 500 of a suitable material, such as a plastic, on which the various microfluidic components are formed. The components can be formed to be formed one or both of the pieces 500, and can be formed to be in or out of fluid communication with one another. As specifically shown in FIG. 22, to enclose the components formed on the pieces 500, a barrier material 502, such as a tape 504, is applied over the microfluidic components on each exposed surface of the pieces 500 in order to enclose the components and form a fluid path along the pieces 500.

The device 10' includes the input well 12 and the second well 26. The input well 12 and the second well 26 are each formed with a downstream extension 200 that includes a pair of converging walls 202 and 204 that extend from a wide end 206 at the downstream end wall 20 of the input well 12 and the downstream end wall 34 of the second well 26 to a narrow end 208 spaced from the downstream walls 20 and 34, respectively.

Instead of connecting to the passages 38 and 79 as in the device 10 of FIG. 1, in the device 10' the narrow end 208 of the extensions 200 from the input well 12 and the second well 26 are each connected to a barrier well 210. The barrier wells 210 are each formed similarly to the second well 26, and receive a predetermined amount of an immiscible isolation buffer or fluid 109 therein, e.g. an oil or wax, as previously described. Again, although barrier wells 210 have a generally rectangular configuration in the depicted embodiment, other shapes and configurations are contemplated without deviating from the scope of the present invention. Each barrier well 210 also includes an extension 200 extending downstream therefrom to connect the barrier well 210 with the immediately downstream well within the device 10'.

As described previously, it is noted that the cross-sectional area of the wide end 206 of each extension 200 is greater than the cross-sectional area of the narrow end 208 of each extension 200, As a result, a biological sample 106 in the input well 12 may flow into the extension 200 through the wide end 206 thereof. However, the surface tension of isolation buffer 109 in the barrier well 210 at the narrow end 208 of the extension 200 of the input well 12 prevents biological sample 106 from flowing into the barrier well 210 through the narrow end 208 of the extension 200. Likewise, the surface tension of reagent 113 in second well 26 at the narrow end 208 of the extension 200 of the barrier well 210 prevents isolation buffer 109 from flowing out of the barrier well 210 into the second well 26. Additionally, the tapering nature of the converging walls 204 and 206 of each extension 200 operates in conjunction with the surface tensions of the various fluids to direct any unbound components of the sample 106 back towards the well through which the bound fraction 110 has moved, it is noted that, similar to other embodiments, the reduced cross-sectional area of the input to the input well 12 pins biological sample 106 within the input well 12 such that inversion of device 10' will not result in biological sample 106 spilling out of input well 12 through the input thereof. Hence, it can be appreciated that device 10' may be rotated and/or inverted to facilitate the mixing of biological sample 106 and the reagent input well 12 or maintain fraction-bound solid phase substrate 110 in suspension.

The second well 26 in addition to having the function described previously, can also be filled with a suitable reagent 113 for providing extracellular staining to the fraction 110 of interest on the solid substrate 111 moved into the second well 26.

Figure 25A:
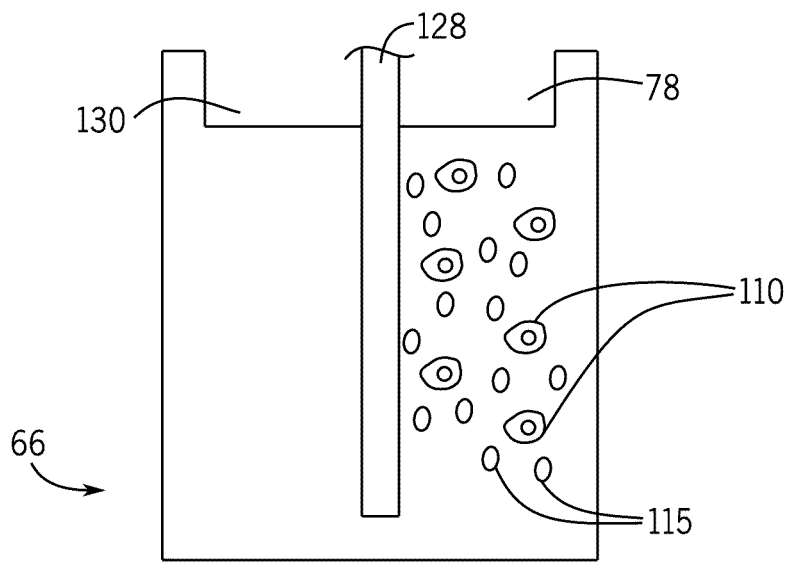
FIGS. 25A-25B are cross-sectional views of the sieve well of FIG. 22 undergoing a PMP removal process.
Figure 25B:
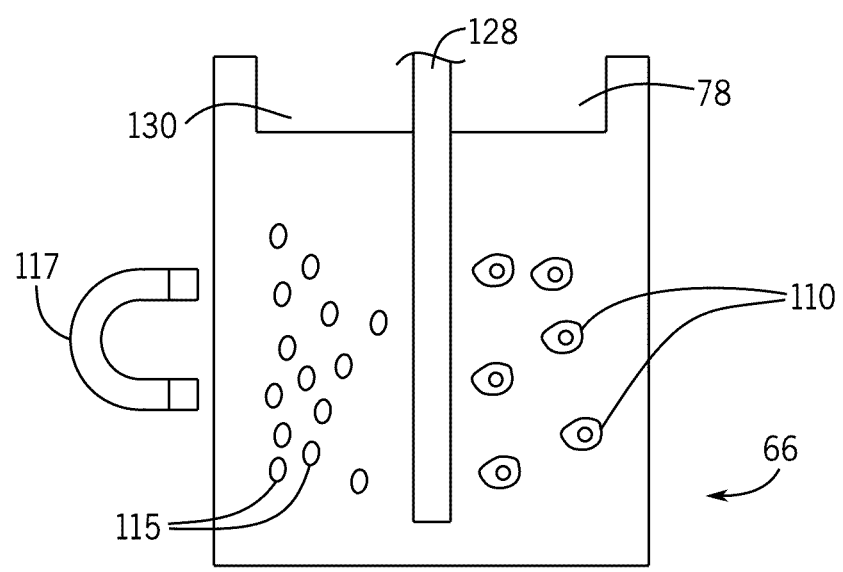

Looking now at FIGS. 21-23A, downstream from the second well 26, the second barrier well 210 is connected to a third or sieve well 66, formed with the third cavity 78 and the replacement cavity 130 separated by a membrane 128 extending across the entire third well 66 and held between the cavities 78 and 130 by a suitable support 131 in the illustrated embodiment. However, in the embodiment of FIGS. 21-23A, the membrane 128 is formed of a dialysis membrane. This type of membrane 128 enables PMP removal from the fraction of interest 110 as the PMPs 115 can traverse the membrane 128 into the replacement cavity 130 under the influence of a the force, e.g., magnet 117, while the fraction 110 is retained within the third cavity 78, as shown in FIGS. 25A-25B. Alternatively, the PMPs 115 can be removed from the fraction 110 using buffers that can cause competitive displacement of the PMPs 115 for removal. With the separated fraction 110 in the third cavity 78, the PMPs in the replacement cavity 130 and the fluid in the third cavity 78 and the replacement cavity 130 can be removed and replaced with additional types of fluids without contacting the fraction 110 disposed in the third cavity 78.

Figure 23A:
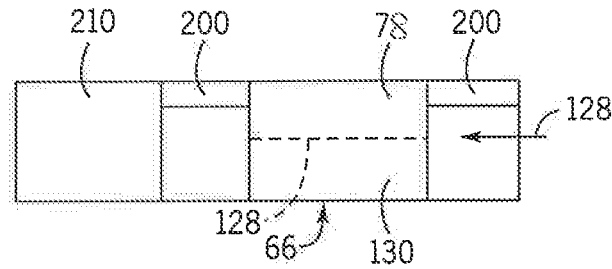
FIG. 23A is a top plan view of the sieve well of FIG. 22.
Figure 23B:
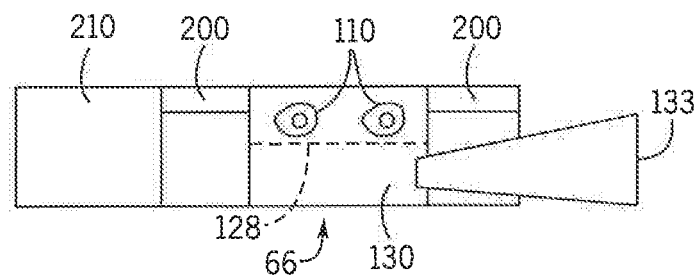
FIG. 23B is a top plan view of the sieve well of FIG. 22 in a first configuration.
Figure 23C:
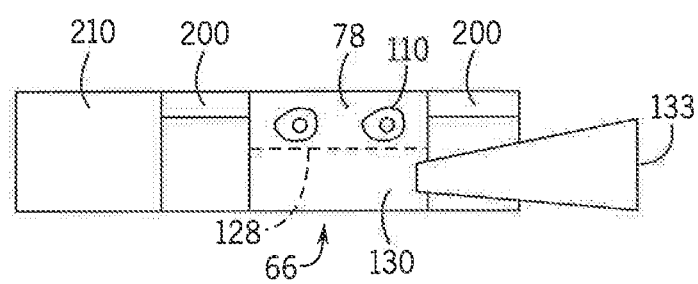
FIG. 23C is a top plan view of the sieve well of FIG. 22 in a second configuration.
Figure 23D:
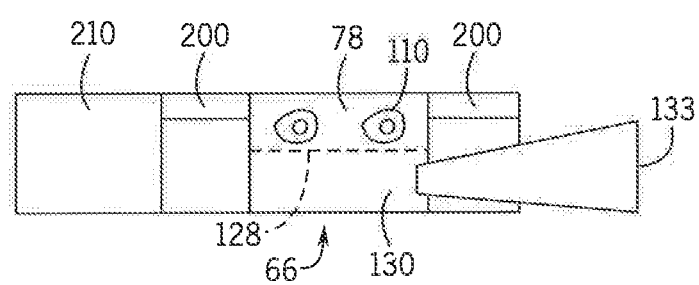
FIG. 23D is a top plan view of the sieve well of FIG. 22 in a third configuration.
Figure 23E:
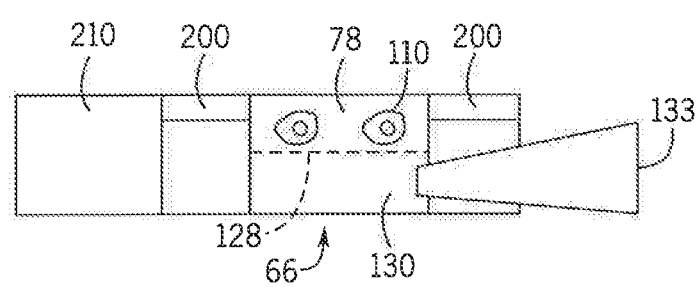
FIG. 23E is a top plan view of the sieve well of FIG. 22 in a fourth configuration.
Figure 24A:
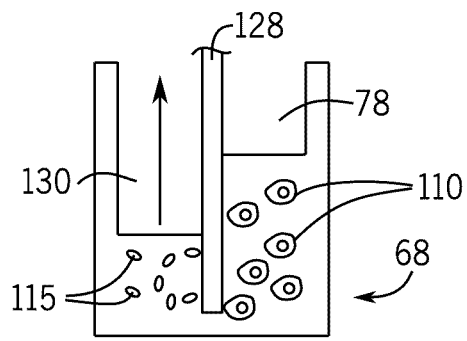
FIGS. 24A-24D are cross-sectional views of the sieve well of FIG. 22 undergoing a fluid transfer process.
Figure 24B:
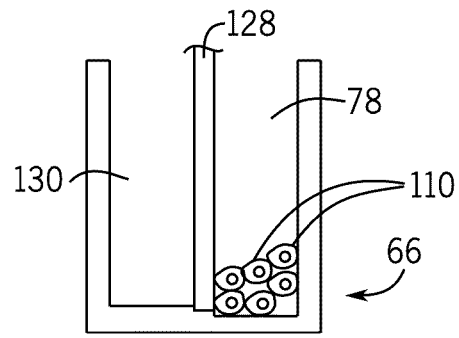
Figure 24C:
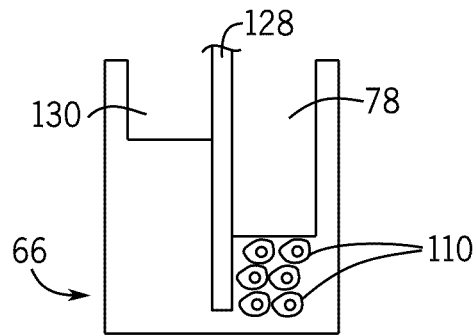
Figure 24D:
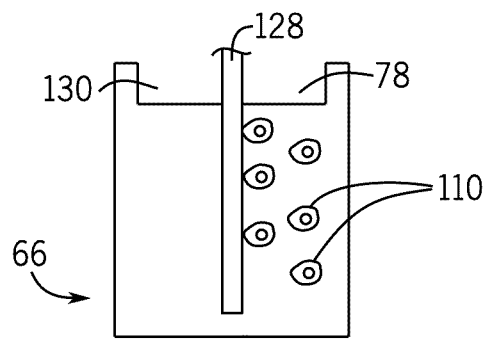

As shown in FIGS. 23B-E, the steps for intracellularly staining the fraction 110 held in the third cavity 78 are illustrated. In each of the steps, it is necessary to remove the fluid present within the third well 66 and replace the fluid with a subsequent fluid, all without directly contacting and damaging the fraction 110 remaining in the third cavity 78 of the third well 66. To do so, as shown in FIGS. 24A-24D, the fluid is removed from the replacement section 130 of the third well 66 via a suitable mechanism, such as aspiration using an aspirator 133 (FIG. 24A). During the removal process, the membrane 128 maintains the fraction 110 within the third cavity 78, until only the fraction 1:10 remains in the third well 66 (FIG. 24B). At this point, a subsequent fluid can be introduced into the third well 66 via the replacement cavity 130 (FIG. 24C), where the fluid will pass through the membrane 128 from the replacement cavity 130 into the third cavity 78 and contact the fraction 110, but without any direct manipulation of the fraction 110 by anything other than the fluid. When the third well 66 has been filled to the desired extent with the subsequent fluid (FIG. 24D), the fluid can be left to act upon the fraction 110 in the desired manner.

Using the method illustrated in FIGS. 24A-24D, initially the PMPs 115 optionally removed from the fraction and the fluid present in the third well 66 are removed, e.g., aspirated, from the third well 66 via the replacement cavity 130. Once the PMPs 115 and fluid have been removed, a wash fluid can be introduced into the replacement cavity 130 to pass through the membrane 128 and contact the fraction 110 held in the third cavity 78 (FIG. 23B). The wash fluid can then be removed from the third well 66 via the replacement cavity 130, and a fluid for fixing the fraction 110 and/or permeabilizing the fraction 110 can be added to the third well 66 (FIG. 23C). The fixing/permeabilization fluid(s) can then be removed from the third well 66 via aspiration from the replacement cavity 130, and a stain of a suitable type can be introduced into the third well 66 via the replacement cavity 130 to pass through the membrane 128 into the third cavity 78 to contact the fraction 110 (FIG. 23D). Once appropriately stained, the staining fluid can be removed from the third well 66 via aspiration from the replacement cavity 130 and a wash fluid can be introduced into the replacement cavity 130 to complete the process (FIG. 23E).

The staining process can be repeated as many times as necessary to complete any number of staining procedures on the fraction 110 held in the third cavity 78. For example, various combinations of different staining techniques using primary and secondary antibodies, e.g., EpCAM-PE, Hoescht, pancytokeratins-FITC, anti-rabbit Androgen Receptor primary antibody with a Alexa488 goat anti-mouse secondary, among others, can be conducted on the cells constituting the fraction 110 disposed within the third cavity 78. Also, as the fraction 110 is never directly contacted during the steps of any technique being utilized, either within the sieve well 66 or during any other step performed in the device 10", the loss of the fraction 110 during the staining procedure steps is greatly minimized.

Once the staining process is completed in the third cavity 78 of the third well 66, the fraction 110 can be imaged to determine various properties of the stained cells constituting the fraction 110. For example, the androgen receptor (AR), which is a high-value therapeutic target in PCa and its misregulation has been linked to drug resistance. Specifically, in-device quantitative immunocytochemistry (ICC) can be employed to measure total AR protein in individual CTCs of the fraction 110, such that we can also evaluate AR heterogeneity within a single patient, Additionally, as a result of the staining process, a cell imaging algorithm can be employed to determine the proportion of AR that has translocated to the cell nuclei, thus enabling delineation of transcriptionally active AR from inactive AR on a CTC-by-CTC basis that may predict evolving resistance mechanisms to AR-targeting therapies.

The imaging of the stained fraction 110 can take place directly within the device 10', either within the third well 66, or in a fourth well 212 located downstream from the third well 66 and formed similarly to the second well 26, but without an extension 200, The fourth well 212 is connected to the third well 66 by a third barrier well 210. The stained fraction 110 can be moved into the fourth well 212 by moving the fraction 110 along the extension 200 of the third well 66, such as by adding additional PMPs (not shown) into the third well 66 to bind to the stained fraction 110 to enable the force to act on and draw the fraction 110 bound to the PMPs into and through the isolation buffer 109 present the third barrier well 210, and from the extension 200 of the third barrier well 210 into a suitable fluid for imaging located in the fourth well 212.

Referring now to FIGS. 26-29B, a further modification of the embodiments of the devices 10 and 10' is illustrated. In this embodiment, the device 10" includes the input well 12, the first channel 38, the second well 26 and the second passage 79 as in the device 10 of FIG. 1. Also, as in the device 10' of FIG. 21, the structure of the device 10" has the reduced cross-sectional area of input to input well 12 to pins biological sample 106 within input well 12 such that inversion of device 10" will not result in biological sample 106 spilling out of input well 12 through the input thereof. Hence, it can be appreciated that device 10" may be rotated and/or inverted to facilitate the mixing of biological sample 106 and the reagent in input well 12 or maintain fraction-bound solid phase substrate 110 in suspension. The device 10" is also formed of the pair of pieces 500 and barriers 502, with the second well 26 also being filled with a suitable reagent for providing extracellular staining to the fraction of interest on the fraction-bound solid substrate 110.

Further, in the device 10", the passages 38 and 79 are each formed with a vertically extending portion 134 that extends from the upper walls 44 and 84, respectively, to the upper surface 21 of the device 10", to provide an entrance for the isolation buffer material, e.g., the oil or wax, forming the barriers provided by the passages 38 and 79.

The device 10" also includes the third well 66 with the membrane 128 separating the third well 66 in a third cavity 78 and a replacement cavity 130. The third well 66 can be operated in the same manner as described with regard to the devices 10 and 10' to provide intracellular staining and analysis of the fraction 110 within the third well 66.

Figure 26:
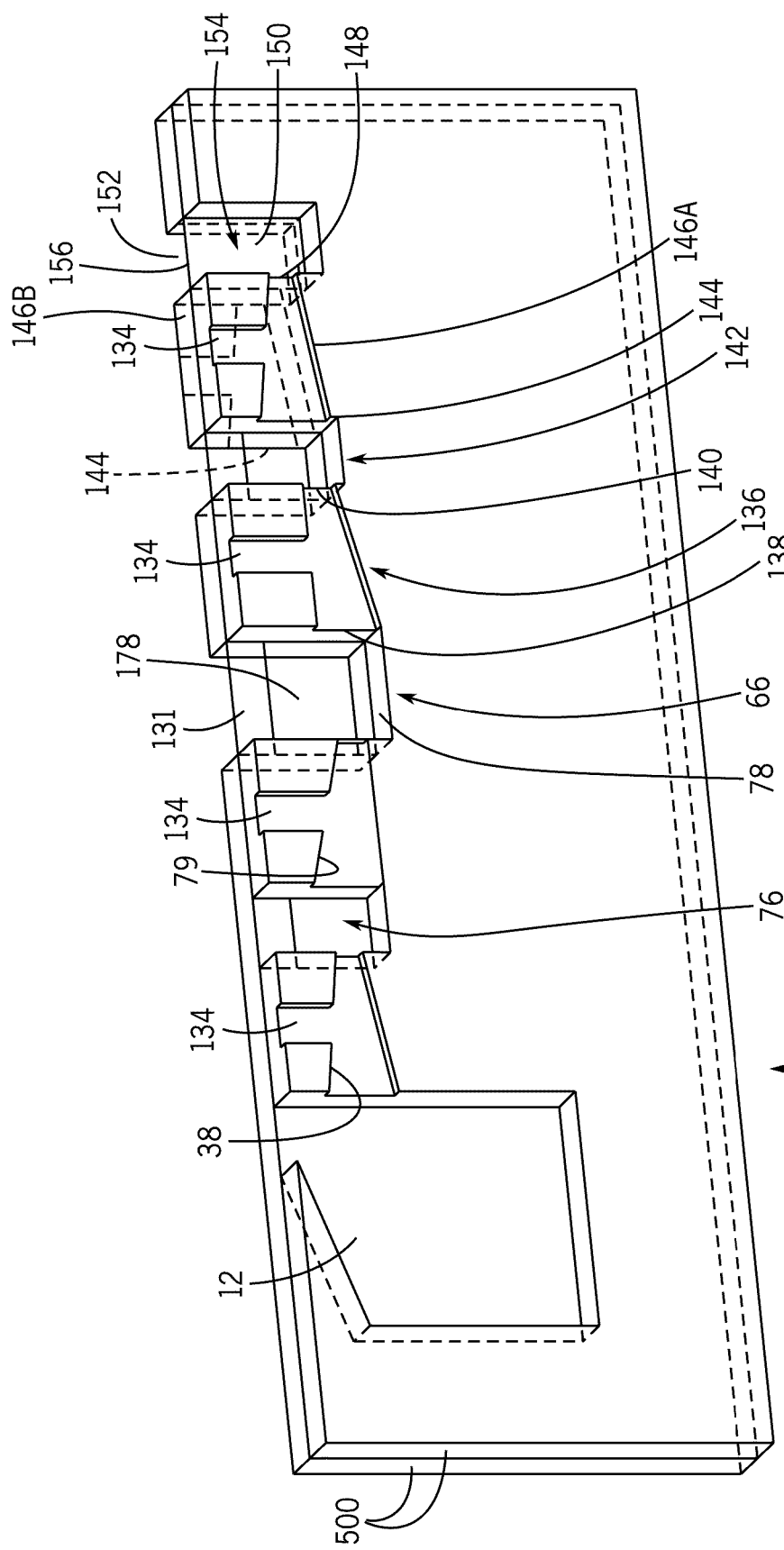
FIG. 26 is an isometric view of a sixth embodiment of the device in accordance with the present invention.

Looking now at FIG. 26, in the device 10" is located a third passage 136 formed similarly to the first passage 38 and the second passage 79 that has an input 138 connected to the third cavity 78 of the third well 66, and an output 140 connected to a fourth or separation well 142. The fourth well 142 is formed similarly to the second well 26 and the third well 66 in the device 10", and is connected opposite the output 140 of the third passage 136 to an input 144 of each of a pair of fourth passages 146A and 146B. The fourth passages 146A and 146B are formed similarly to the first, second and third passages 38, 79, and 136 and are disposed on opposed sides 17 and 19 of the device 10". Each fourth passage 146A and 146B additionally has an output 148 that is connected to one cavity 150 or 152 of a fifth or elution well 154. The fifth well 154 is formed similarly to the third well 66 and fourth well 142, with the fifth well 154 including a solid barrier 156 therein completely separating the cavities 150 and 152 formed on opposed sides of the fifth well 154.

Figure 27:
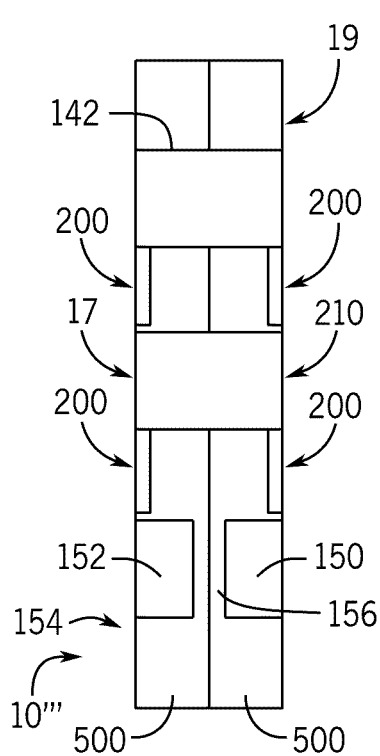
FIG. 27 is a top plan view of a separation well, barrier well and elution well of the device of FIG. 26 is a second configuration.

In an alternative and simplified configuration of the device 10''' shown in FIG. 27, the separation well 142 functions as an input well and is formed with a pair of extensions 200 disposed on opposed sides 17 and 19 of the device 10'''. These extensions 200 are connected at the narrow ends 208 to a barrier well 210, which also has a pair of extensions 200 disposed on opposed sides 17 and 19 of the device 10''' extending downstream therefrom. The narrow ends 208 of the extensions 200 of the barrier well 210 are connected to one of the cavities 150, 7152 formed in the elution well 154.

Figure 28A:
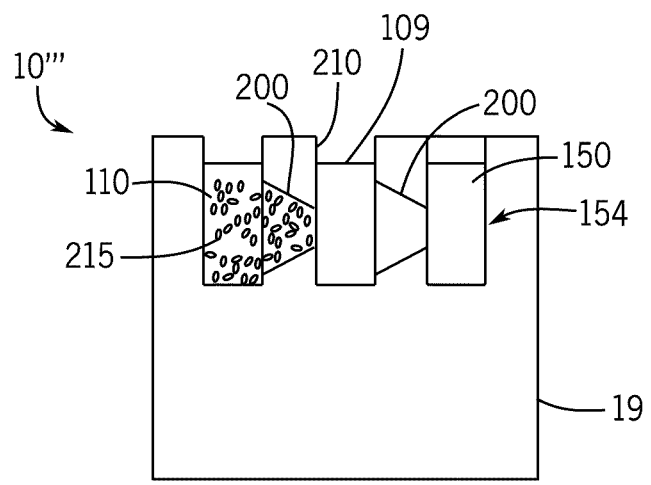
FIGS. 28A-28C, are side plan views of the extraction of mRNA from a sample in the separation well of FIG. 27.
Figure 28B:
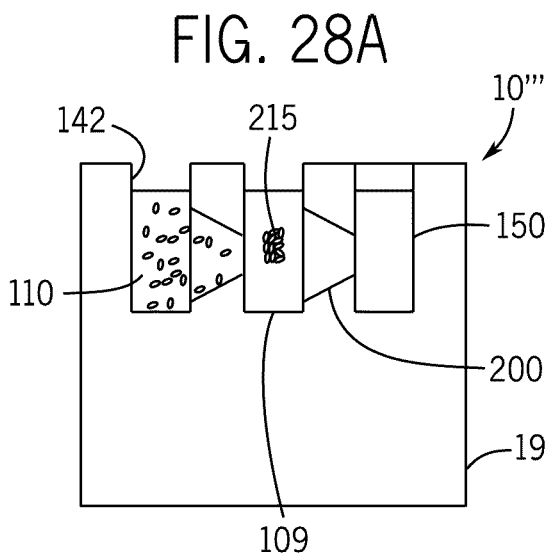
Figure 28C:
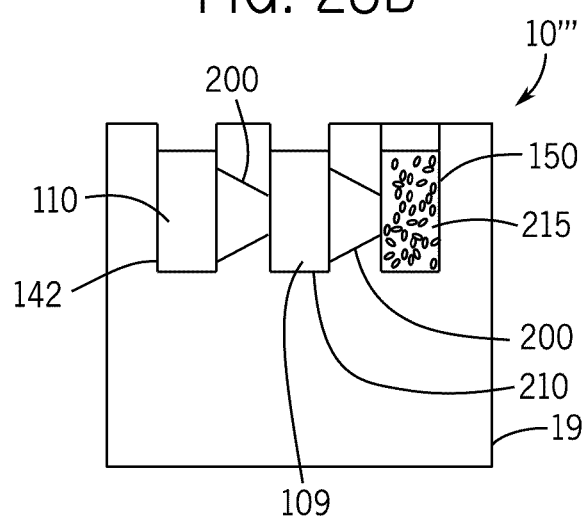
Figure 29A:
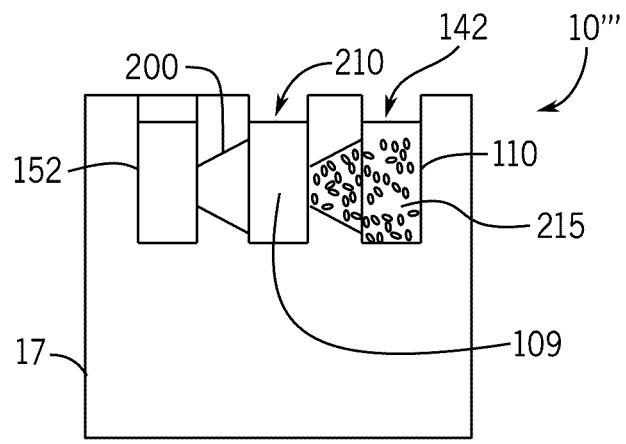
FIGS. 29A-29C are side plan views of the extraction of DNA from a sample in the separation well of FIG. 27.
Figure 29B:
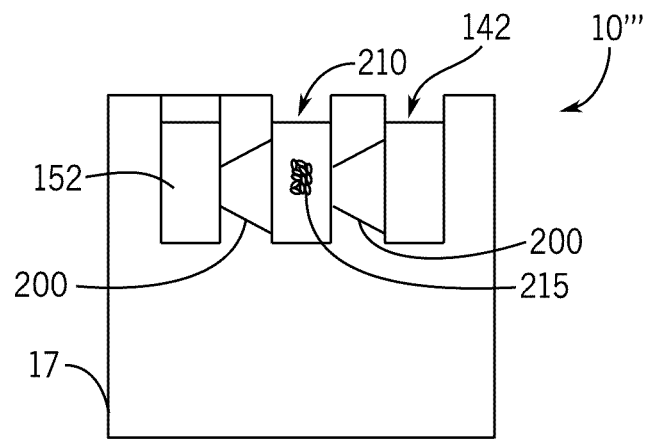

Referring now to FIGS. 28A-28C and 29A-29C, in use of either embodiment of the device 10" or 10''', when the fraction 110 has been moved into after performing the protein analysis in the sieve or third well 66 or placed within the separation well 142, the fraction 110 can be resampled or repeatedly interrogated by sequentially adding paramagnetic particles (PMPs) 215 of varying chemistries and different lysis buffers to the separation well 142 to isolate either the mRNA or DNA from the same cells constituting the fraction 110 without the need for splitting the fraction 110 (FIGS. 28A and 29A). Once extracted from the fraction 110, the mRNA or DNA and associated PMPs 215 can be moved through the isolation buffer 109 by a magnetic force through the respective passage 146A or 146B or barrier well 210 and extension 200 into the appropriate cavity 150 or 152 (FIGS. 28B and 29B), Within the cavity 150 or 152, the mRNA or DNA is released from the PMPs 215 (FIGS. 28C and 29C) to enable further analysis of the mRNA or DNA, and the fraction 110 remaining in the fourth well 142 can be further interrogated for the mRNA or DNA remaining in the fraction 110. When extracting both mRNA and DNA from the fraction, the steps of FIGS. 28A-28C are performed first to extract the mRNA from the fraction 110, with a subsequent extraction of the DNA according to the steps illustrated in FIGS. 29A-29C.

From the cavities 150 and/or 152 in the fifth well 154, the extracted mRNA can be used to quantify AR gene expression and the DNA probed for AR gene mutations. The flexibility of this assay extends beyond AR-focused assays to include any protein, DNA and/or mRNA target of interest. As such, this CTC functional assay employing the device 10 can be used as a companion biomarker assay for nearly any molecular targeting therapy as they can be captured from blood replacing painful and expensive biopsies and permitting more frequent testing. Future directions for this device 10 and use in this and other types of CTC assays include integration with existing automated liquid handlers, thus enabling high-throughput patient processing for a much broader range of diseases and therapies, including characterization of CTCs for disease prognosis and personalized treatment; circulating fetal cells for prenatal diagnosis; T-cells for immune monitoring; and stem cells for analysis of biochemical and developmental processes.

EXPERIMENTAL

Fabrication

A simplified device 10''' including a separation well 142, a barrier well 210 and an elution or fifth well 154 separated into a first cavity 150 and a second cavity 152 as illustrated in FIG. 27 was constructed. The device 10''' was manufactured from pieces 500 formed of 2 mm thick polystyrene (PS, Goodfellow, UK) using a CNC mill (PCNC770, Tormach, USA). The separation well 142 and barrier well 210 consisted of two through holes, 3 mm in width and 5 mm in height. The elution well 154 has the same dimensions with a 1.5 mm depth. Each well 142, 210 and 154 was connected by a trapezoid passage extension 200 with a height ranging from 2 mm down to 0.8 mm and was milled to a depth of 0.3 mm. The back piece 500, formed of the same material as the front piece 500, was mirrored based on the front piece 500. The front and back pieces 500 were solvent bonded (Weak solvent based chip lamination, Zhou, 2010) so that the separation well 142 and barrier well 210 had an approximate volume of 40-60 µL and the elution well 154 had an approximate volume of 15-20 µL. A pressure sensitive adhesive 504 (MicroAmp, Applied Biosystems, USA) was then applied to the front and back of the device 10''' over the wells 142, 210 and 154 and the extension 200 to form outer walls on the device 10''' to contain the fluids within the wells 142, 210 and 154 and the extensions 200.

Operation

Figure 29C:
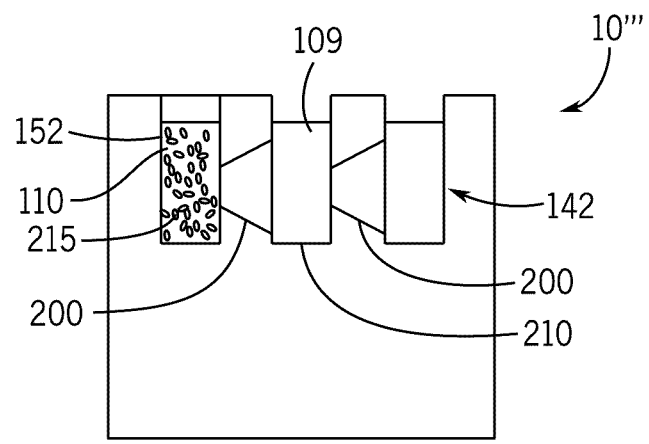

The device 10''' uses immiscible filtration assisted by surface tension to extract and purify mRNA and DNA from the same sample. To operate the device 10''', PMPs 215 functionalized with olgio(dt)'s and a lysis buffer optimized to bind mRNA are added to the input well 142 containing the sample 110 (FIG. 28A). Following mRNA binding, a simple handheld magnet draws the PMPs 215 along the front of the device 10''' through the barrier well 210 containing silicon oil (FIG. 28B) to the front cavity 150 of the output well 154, where the mRNA s released from the PMPs 215 (FIG. 28C). Next, silica PMPs 215' and a lysis buffer optimized to bind DNA are sequentially added to the input well 142 containing the remainder of the sample 110 (FIG. 29A). Following DNA binding, the PMPs 215' are moved from the input well 142 along the backside of the device 10''' through the barrier well 210 and routed to the separated back cavity 152 of the output well 154 (FIG. 29B) where the DNA can be released from the PMPS 215' (FIG. 29C). Samples of the mRNA and the DNA extracted from the sample 110 can then be collected from the respective cavities 150, 152 and used for a variety of downstream assays. Since this technique avoids the use of dilutive or centrifugation steps, it is ideal for rare samples as the original sample 110 is unperturbed and available for further interrogation.

More particularly, in this method 15 of nuclease free water was added to both cavities 150 and 152 of the elution well 154. Next, 10 µL of cells suspended in 1×PBS was added to the separation well 142, followed by 15 µL mRNA lysis/binding buffer, referred to as LIDS 2, (10 mM Tris-HCL, 500 mM LiCl, 1% Igepal® CA-640 (Sigma-Aldrich, USA), 5 mM EDTA, 1 mM DTT, pH 7.5) containing 30 µg olgio(dt)$_{25}$ Dynabeads® (Life Technologies, USA)) as PMPs 215. To complete filling, 40 µL, silicon oil (Fisher, USA) was added to the barrier well 210. After, 5 minutes the olgio(dt)$_{25}$ PMPs 215 were transferred from the separation well 142 through the barrier well 210 along the front of the device 10''' to the front cavity 150 of the elution well 154 using a permanent magnet (B333-N52 K&J Magnetics).

Next, 25 µL of DNA lysis/binding buffer (10 mM Tris-HCL, 6 M GTC, 0.1% Igepal® CA-640, pH 7.5) containing 1 µL MagneSil® PMPs 215' (Promega, Madison) was added to the separation well 142 containing the cells. After 5 minutes the MagneSil® PMPs were transferred from the separation well 142 through the barrier well 210 along the rear of the device 10''' to the rear cavity 150 of the elution well 154 using a permanent magnet. The elution buffers with PMPs were collected for further downstream analysis, Real Time—Polymerase Chain Reaction Analysis Unless otherwise stated, the mRNA elution sample containing PMPs was reverse transcribed using a High Capacity cDNA Reverse Transcript kit (ABI, Foster City, Calif.) according to manufactuer's directions. For PSA and AR mRNA gene expression assays, 4 µL of template was mixed with 10 µL, LightCycler 480® probes master mix (Roche, USA), 0.3 µM forward and reverse primers, 0.2 µM probes (Universal Probe Library, Roche, USA) and 5.2 µL NF water (Primers and probes specified in S1). For all other gene expression assays, 1 µL TaqMan® Gene Expression Assay (Life Technologies, USA) replaced the primers and probes used previously (TaqMan® Gene Expression Assays specified in S1). Each reaction was amplified for 50 cycles (denatured at 95° C. for 15 seconds followed by annealing at 60° C. for 1 minute) using a LightCycler® 480 Real Time PCR System (Roche, USA). Relative gene expression levels were quantified using delta $C_t$ method.

Cell Culture

For use as the sample 110, prostate cancer epithelial cells (LNCaPs) were cultured at 37° C. and maintained under 5% $CO_2$ in polystyrene flasks until confluent in Cornig Cellgro® RPMI 1640 Medium (VWR) containing 10% fetal bovine serum (Gibco®). 1% Pen Strep (Gibco®), 1% MEM-non-essential amino acids (Gibcoe) and 1% NaPyruvate (Cornig Cellgro®) Cells were released using a 0.05% trypsin/EDTA solution and collected via centrifugation.

Lysis Buffer Optimization

Three separate lysis buffers were evaluated to determine the best nucleic acid binding capacity. The protocol for operation of the device 10''' was performed as described above except different mRNA lysis buffers were interchanged including; lx RIPA buffer (Milipore), LIDS 1 (Life Tech) and a less stringent LIDS 2 buffer. The only difference of the LIDS 2 buffer from the commercially available LIDS 1 buffer is the replacement of the ionic detergent lithium dodecyl sulfate (LDS) with a nonionic detergent Igepal® CA-640. GAPDH gene expression assays were performed on both mRNA and DNA. Relative gene expression levels were determined and a two-tailed t-test performed for comparison of each mRNA lysis buffer with p<0.005 considered significant.

Comparison of the Device 10''' to Qiagen AllPrep DNA/RNA Microextraction Kit A 1:10 serial dilution of 100,000 to 100 LNCaPs/mL of 1×PBS was performed on two separate days. 10 µL of each serial dilution (n=2) was processed using the device 10''', which correlated to 1000, 100, 10 and 1 LNCaP per a device. 10 µL of the same serial dilutions were added to 65 µL RLT buffer and processed according to Qiagen AllPrep DNA/RNA Micro Kit manufacturer's directions. For all samples containing 100 cells or less, carrier RNA was added. A control sample containing no cells was also performed to assess for possible NA contamination. Relative gene expression levels were determined for GAPDH, AR and PSA on both DNA and mRNA.

Results & Discussion

Lysis Buffer Optimization

Figure 30:
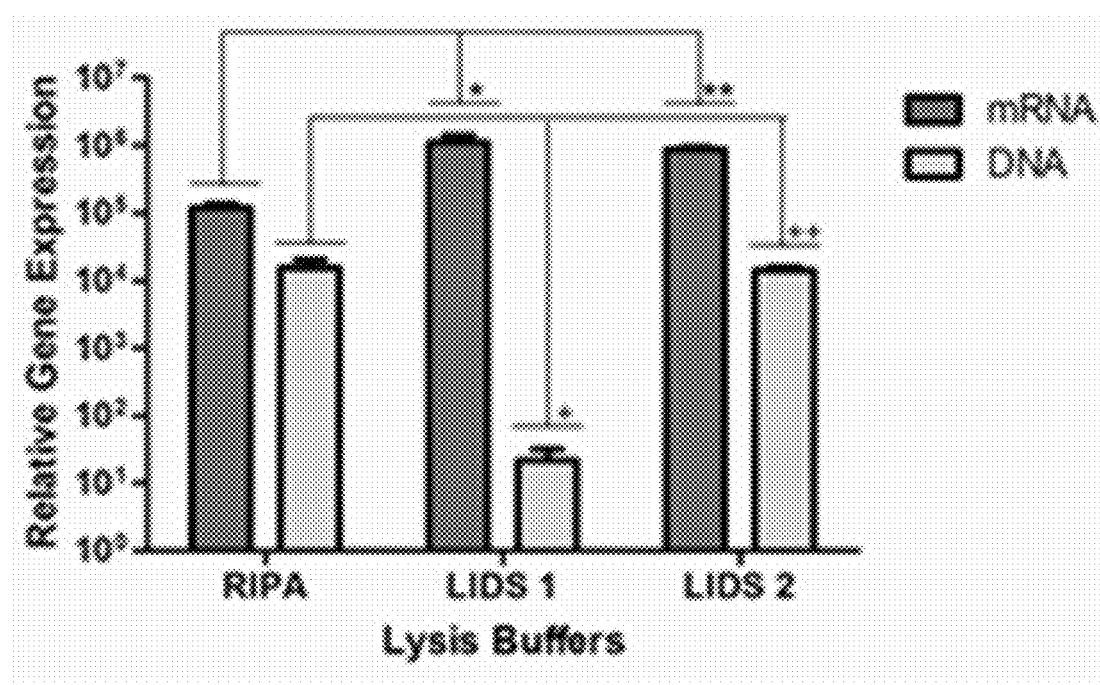
FIG. 30 is a graph of relative mRNA and DNA GAPDH expression for the comparison of different mRNA lysis buffers.

To achieve maximum mRNA and DNA extraction efficiency, three different lysis buffers were evaluated using the device 10''' and the relative GAPDH gene expression from 1000 LNCaPs determined. GAPDH gene expression was used because traditional methods to determine purity and amount (Agilent Bioanlayzer, nanodrop & flourimeter) were not applicable for the limited amount of material isolated from rare cells. As shown in FIG. 30, use of both LIDS 1 and LIDS 2 resulted in a higher relative mRNA GAPDH expression as compared to the RIPA. While no statistical significance between LIDS 1 and LIDS 2 (p>0.513) was calculated there was a significant difference between both LIDS 1 (p<0.028) and LIDS 2 (p<0.001) with RIPA. The relative increase in GAPDH mRNA expression could be due to the differences and concentrations of salts used in the RIPA (150 mM NaCl) as compared to the LIDS 1 & 2 (500 mM LiCl).

Additionally, FIG. 30 shows higher relative GAPDH DNA expression for use of RIPA and LIDS 2 as compared to LIDS 1. In this case, a statistical difference was seen between LIDS 1 with both RIPA (<0.039) and LIDS 2 (p<0.001), however no statistical difference was seen between RIPA and LIDS 1 (p>0.794). Physical examination revealed clumping between the DNA PMPs when LIDS 1 was used. This could be due to the ionic detergent lithium dodecyl sulfate (LDS) used in LIDS 1 binding to the PMPs resulting in competitive binding with DNA. To circumvent this issue, the ionic LDS detergent was replaced with the non-ionic detergent Igepal CA-360 in LIDS 2 to achieve efficiency comparable to RIPA. For DNA lysis buffers, two different buffers containing either 6 M or 8 M guanidinium thiocyanate (GTC) were tested with no difference seen (data not included). In addition, the 8 M GTC buffer was difficult to keep in solution and made operation difficult due to salt precipitation when the devices were kept on ice. Based on optimization in the device 10''' of the mRNA lysis buffer, LIDS 2 was used with the 6 M GTC DNA binding buffer.

Comparison of the Device 10''' to Qiagen AllPrep DNA/RNA Micro Kit

A Qiagen Allprep DNA/RNA Micro kit as a benchmark to the device 10''' as it is to the most widely used and sensitive technique. To asses for possible NA contamination, a control sample containing no cells was processed. The results of this comparison are shown in FIG. 31 where column A) illustrates a comparison of GAPDH, AR and PSA relative mRNA expression purified from 1000, 100, 10 or 1 LNCaPs using the device 10''' (Integrated VerIFAST) or the Qiagen Allprep DNA/RNA Micro kit, and column B) is illustrates the comparison of GAPDH, AR and PSA relative DNA expression purified from 1000, 100, 10 or 1 LNCaPs using the device 10''' (Integrated VerIFAST) or the Qiagen Allprep DNA/RNA Micro kit, Each dot represents an individual experiment NA purification procedure using either the device 10''' (grey) or Qiagen (black) with the horizontal lines representing the mean of the individual experiments.

Figure 31:
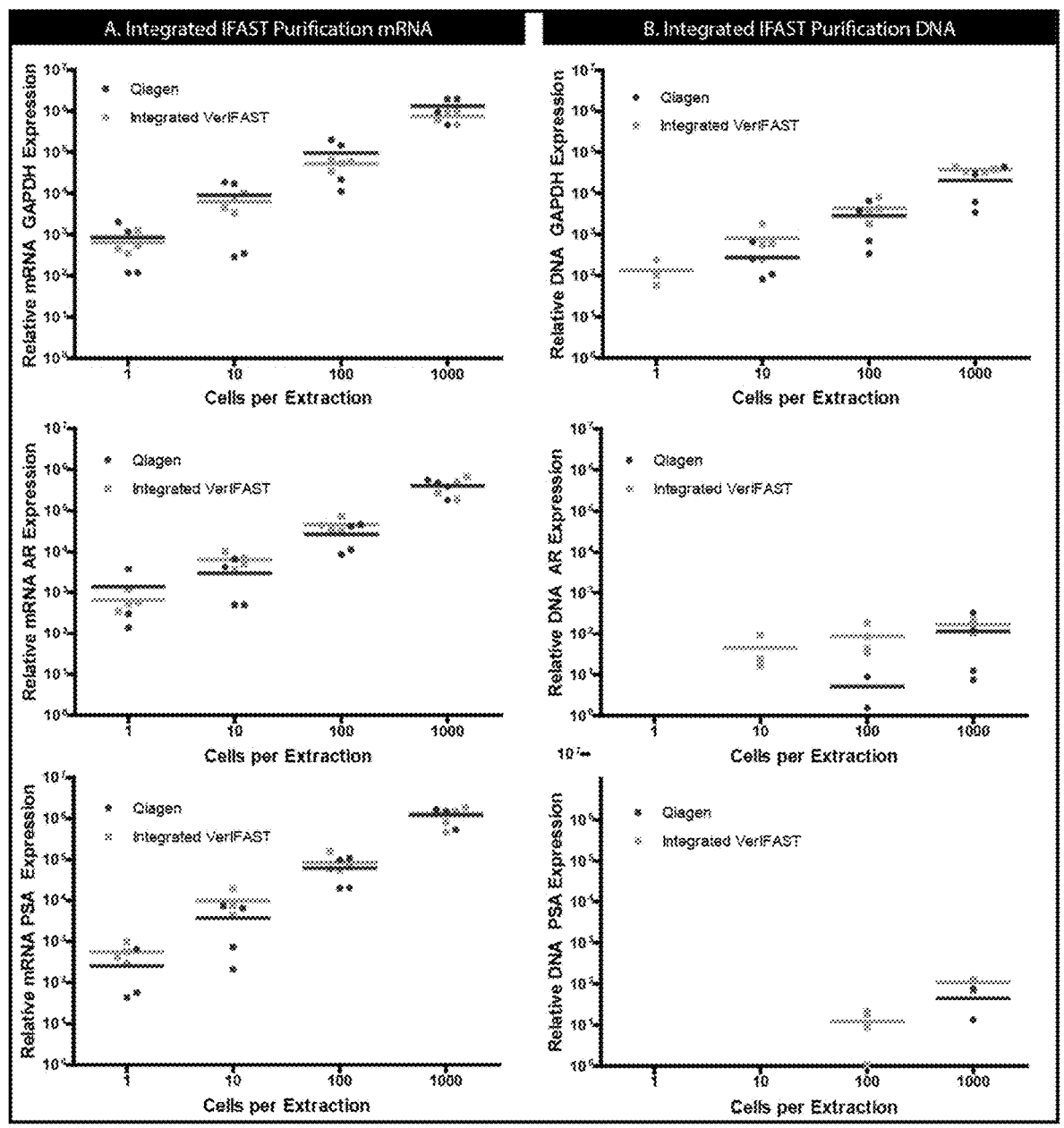
FIG. 31 are graphs of the: A) Comparison of Glyceraldehyde-3-phosphate dehydrogenase (GAPDH), androgen receptor (AR) and prostate-specific antigen (PSA) relative mRNA expression purified from 1000, 100, 10 or 1 LNCaPs using Device 10''' or Qiagen Allprep DNA/RNA Micro Kit; and the B) Comparison of GAPDH, AR and PSA relative DNA expression purified from 1000, 100, 10 or 1 LNCaPs using Device 10''' or Qiagen Allprep DNA/RNA Micro Kit.

FIG. 31 shows that the device 10''' achieved higher relative mRNA and DNA expression levels compared to the Qiagen kit. In column A, using the device 10''', mRNA purification and relative gene expression for GAPDH, AR and PSA is at 100% of single cell samples. Using the Qiagen kit we show mRNA purification and relative gene expression for GAPDH in 100% of single cell samples and AR and PSA in only 75% of single cell samples. Higher variability in mRNA isolation was also observed for the Qiagen technique as LNCaP numbers decreased, with the average coefficient of variance being 48.7±15.1% for Qiagen and 28.9±7.0% for the device 10'''. This could be due to sample lost through additional fluid transfer steps, centrifugal forces that result in fluid shear stresses and partial elution in wash buffers.

In column B of FIG. 31, using the device 10''' we show DNA purification and relative gene expression for GAPDH in 75% of single cell samples. AR gene expression is reduced to 75% for 10 cell samples and PSA gene expression to 75% for 100 cell samples. The higher sensitivity of GAPDH DNA expression could be due to copy number aberrations from aberrant karyotypes in LNCaPs, a feature common to cancer cell lines. For AR and PSA, the lower sensitivity could also be due to primer design, especially for PSA as there are three different isoforms. For the Qiagen technique no GAPDH gene expression was observed for a single cell. AR gene expression was reduced to 50% for 100 cell samples and PSA gene expression to 50% for 1000 cell samples. The efficiency of mRNA and DNA GAPDH gene expression using a standard curve was also confirmed.

Finally, to show the utility of the device 10''' for the genomic and transcriptomic analysis of rare cell populations, we isolated CTCs from two prostate cancer patients. These cells were processed using the device 10''' and detection of GAPDH and AR gene expression achieved by RT-PCR. Within both of these patient samples, we were able to detect GAPDH and AR for both DNA and mRNA, as shown in Table 1.

TABLE 1

GAPDH and AR relative mRNA and DNA expression from nucleic acids purified using the Device 10''' from CTCs in two different patients diagnosed with prostate cancer.

| Patient # | CTC # | Relative DNA Expression | | Relative mRNA Expression | |
|---|---|---|---|---|---|
| | | GAPDH | AR | GAPDH | AR |
| 1 | 47 | 27746.2 | 1002.9 | 23821.9 | 251465.3 |
| 2 | 7 | 25709.3 | 94.4 | 3304.0 | 121.9 |

DNA gene expression values they were higher due the contaminating PBMCs that also express GAPDH and AR. However, while mRNA GAPDH will be expressed in both CTCs and PBMCs, AR should only be expressed by the CTCs. We were also to obtain sequencing data of the AR PCR product amplified from mRNA.

The devices 10, 10', 10", 310, 360 and 420 rely on immiscible phase exclusion and significantly reduce dilutive and centrifugation processes that likely result in sample loss due to increased fluid manipulation and purification time. While effective for rare cell purification, the devices 10, 10', 10", 310, 360 and 420 could be scaled for use with larger samples.

Further the devices 10, 10', 10", 310, 360 and 420 can be utilized in techniques for mRNA and DNA purification from a single cell. In addition, the devices 10, 10', 10", 310, 360 and 420 and their associated methods of use have the ability to integrate with several previously developed microfluidic devices for rare cell isolation enabling molecular interrogation of these cells. In particular, the devices 10, 10', 10", 310, 360 and 420 and their method of use has potential for utilization in whole genome and transcriptome amplification, DNA and RNA sequencing and microarray applications to expand the versatility of molecular assays that can be performed using the devices 10, 10', 10", 310, 360 and 420.

In alternative embodiments of the devices 10, 10', 10", 10''', 310, 360 and 420, the various wells and passages in the devices are not fully filled with the desired fluid in order to prevent spillage of the fluids during processing of a biological sample 106, and also the enable manipulation of the sample 106 or fraction 110 within the various wells and/or passages.

Also, the fraction 110 can be isolated from the sample 106, and can then be subsequently further fractionated to separate parts or portions of the isolated fraction 110 from one another. This further fractionation or separation of the cells of the initial isolated fraction 110 can be done within the device 10, 10', 10", 10''', 310, 360 or 420, all without diluting, removing, splitting or otherwise directly disturbing the fraction 110 or any component thereof. By enabling the separation of the fraction 110 and any subsequent sub-fractions therefrom in this manner, the integrity of the fraction 110 and any subset thereof is maintained to allow for multiple assays to be conducted on a single fraction 110 or subset thereof.

Additionally, in order to reduce the interference with the separation of the fraction 110 from the sample 106, it is contemplated to introduce secondary components into the wells 12 and 23, such as agarose beads, among others, that are capable of attaching to any background cells in the sample 106, such as leukocytes, that are desired to be removed from the biological sample 106. The secondary components can then be moved, along with the attached leukocytes, to a location in the input well 12 or droplet where the leukocytes do not interfere with the isolation of the fraction 110. The secondary components for removal of these background cells can also be disposed within other wells or droplets in the devices to assist in reducing interference with any leukocytes the exit the input well with the fraction 110 and substrate 111. In addition, further isolation wells and/or barrier droplets, passages or wells can be added to the devices 10, 10', 10", 10'", 310, 360 and 420 in order to increase the gravitational settling and isolation capabilities of the devices 10, 10', 10", 10'", 310, 360 and 420. Further, various filters and other structural barriers can be added to the devices 10, 10', 10", 10'", 310, 360 and 420 to provide additional isolation capabilities.

Further, the devices 10, 10', 10", 10'", 310, 360 and 420 can be employed in various assay methods that use blood samples collected from an individual or mammal as the source of the biological sample for the assay. The blood samples can be collected, separated to obtain the biological sample, such as by density centrifugation, and prepared for use in the devices by adding the appropriate PMPs to the biological sample obtained. The sample and PMPs can then be introduced into one of the various devices 10, 10', 10", 10'", 310, 360 and 420 in order to perform the assay for that sample.

Various modes of carrying out the invention are contemplated as being within the scope of the following claims particularly pointing out and distinctly claiming the subject matter, which is regarded as the invention.

We claim:

1. A method of conducting an assay on a fraction of cells in a biological sample, the method comprising the steps of:
    a) obtaining a biological sample;
    b) binding a solid phase substrate to a fraction of the sample;
    c) isolating the fraction from a remainder of the sample in a device by applying a force to the solid phase substrate to form an isolated fraction, wherein the device includes a well having a first cavity and a second cavity and a fluid-permeable membrane extending across the well between the first cavity and the second cavity, wherein the applied force forms the isolated fraction in the second cavity of the device and wherein the fluid-permeable membrane enables the exchange of fluids in the well surrounding the isolated fraction disposed in the second cavity from the first cavity without transferring the isolated fraction from the second cavity to the first cavity; and
    d) conducting at least a part of at least one of a protein, genomic and gene expression analysis on the isolated fraction within the device, wherein the step of conducting at least a part of at least one of a protein, genomic and gene expression analysis on the isolated fraction comprises the steps of:
        i) contacting the isolated fraction disposed within the second cavity of the well with a first fluid introduced into the first cavity of the well; and
        ii) contacting the isolated fraction with a second fluid, wherein the step of contacting the isolated fraction with the second fluid comprises:
            e) withdrawing the first fluid via the first cavity and from the second cavity in which the isolated fraction is situated through the fluid-permeable membrane; and
            f) introducing the second fluid into the first cavity of the well and into the second cavity through the fluid-permeable membrane.

2. The method of claim 1 wherein the isolated fraction within the second cavity is directly contacted within the device only by the first fluid and second fluid introduced into the first cavity.

3. The method of claim 1 wherein the step of isolating the fraction comprises isolating a fraction having 1000 cells or less.

4. The method of claim 1 wherein the step of conducting at least one of a protein, genomic and gene expression analysis on the isolated fraction comprises conducting a protein analysis on the isolated fraction.

5. The method of claim 4 wherein the protein analysis is conducted in part by staining the isolated fraction within the device.

6. The method of claim 5 wherein the first fluid is introduced to fix and permeabilize the isolated fraction; and wherein the second fluid is introduced to stain a selected component of the isolated fraction.

7. The method of claim 6 further comprising the step of imaging the stained isolated fraction within the device.

8. The method of claim 1 wherein the step of conducting at least a part of at least one of a protein, genomic and gene expression analysis on the isolated fraction comprises conducting a gene expression analysis on the isolated fraction.

9. The method of claim 8 wherein the step of conducting the gene expression analysis comprises the steps of:
    g) extracting mRNA from the isolated fraction within the device to form extracted mRNA, and
    h) conducting an analysis on the extracted mRNA.

10. The method of claim 9 further comprising the step of conducting a genomic analysis on the isolated fraction after extracting the mRNA.

11. The method of claim 10 wherein the step of conducting the genomic analysis on the isolated fraction comprises the steps of:
    i) extracting DNA from the isolated fraction within the device to form extracted DNA; and
    j) conducting an analysis on the extracted DNA.

12. The method of claim 11 wherein the mRNA and DNA are extracted from the same isolated fraction.

13. The method of claim 12 wherein the isolated fraction is a single cell.

14. The method of claim 1 wherein the biological sample is a blood sample.

15. The method of claim 14 wherein the isolated fraction of the biological sample is formed of circulating tumor cells.

16. The method of claim 1 further comprising the step of isolating a portion of the isolated fraction after the step of isolating the fraction.

17. The method of claim 1 further comprising the step of separating background cells in the sample from the fraction after binding the fraction to the solid phase substrate.

18. The method of claim 1 wherein the isolated fraction is a first isolated fraction, and further comprising the steps of:
    k) binding a solid phase substrate to a second isolated fraction of the sample after isolating the first isolated fraction from the remainder of the sample;
    l) isolating the second isolated fraction from the remainder of the sample in the device by applying a force to the solid phase substrate to form a second isolated fraction; and m) conducting at least a part of at least one of a protein, genomic and gene expression analysis on the second isolated fraction within the device.

\* \* \* \* \*